United States Patent [19]
Antanavich et al.

[11] Patent Number: 5,788,662
[45] Date of Patent: Aug. 4, 1998

[54] METHODS FOR MAKING CONCENTRATED PLASMA AND/OR TISSUE SEALANT

[75] Inventors: Richard D. Antanavich, Paso Robles; Randel Dorian, Orinda, both of Calif.

[73] Assignee: Plasmaseal LLC, San Francisco, Calif.

[21] Appl. No.: 736,862

[22] Filed: Oct. 22, 1996

Related U.S. Application Data

[63] Continuation of Ser. No. 351,010, Dec. 7, 1994, Pat. No. 5,585,008.

[51] Int. Cl.$^6$ .......................... A61K 35/16; B10D 61/24
[52] U.S. Cl. ..................... 604/6; 604/4; 210/782; 422/44; 494/31; 494/33; 494/36; 494/45; 424/530
[58] Field of Search .................. 210/782; 422/44; 494/31, 33, 36, 45; 604/4, 6; 424/530

[56] References Cited

U.S. PATENT DOCUMENTS

| | | |
|---|---|---|
| 3,441,143 | 4/1969 | Kudlaty ............................ 210/333 |
| 3,453,364 | 7/1969 | Flodin et al. ....................... 424/180 |
| 3,972,812 | 8/1976 | Gresl, Jr. ........................... 210/77 |
| 4,059,108 | 11/1977 | Latham, Jr. ..................... 128/214 R |
| 4,225,580 | 9/1980 | Rothman et al. .................... 424/78 |
| 4,294,707 | 10/1981 | Ikeda et al. ....................... 210/782 |
| 4,298,598 | 11/1981 | Schwarz et al. .................... 424/101 |
| 4,300,717 | 11/1981 | Latham, Jr. ....................... 233/1 A |
| 4,303,193 | 12/1981 | Latham, Jr. ...................... 233/23 A |
| 4,322,298 | 3/1982 | Persidsky ........................ 210/787 |
| 4,377,572 | 3/1983 | Schwarz et al. .................... 424/101 |
| 4,414,976 | 11/1983 | Schwarz et al. .................. 128/334 R |
| 4,424,132 | 1/1984 | Iriguchi ........................... 210/800 |
| 4,427,650 | 1/1984 | Stroetmann ........................ 424/46 |
| 4,427,651 | 1/1984 | Stroetmann ........................ 424/46 |
| 4,442,655 | 4/1984 | Stroetmann ......................... 53/428 |
| 4,446,021 | 5/1984 | Aufderhaar et al. ................. 210/378 |
| 4,453,939 | 6/1984 | Zimmerman et al. ................. 604/368 |
| 4,537,767 | 8/1985 | Rothman et al. .................... 424/78 |
| 4,627,879 | 12/1986 | Rose et al. ........................ 106/124 |
| 4,631,055 | 12/1986 | Redl et al. ......................... 604/82 |
| 4,632,761 | 12/1986 | Bowers et al. ..................... 210/650 |
| 4,639,316 | 1/1987 | Eldegheidy ...................... 210/416.1 |
| 4,655,211 | 4/1987 | Sakamoto et al. ................... 128/156 |
| 4,672,969 | 6/1987 | Dew .............................. 128/397 |
| 4,714,457 | 12/1987 | Alterbaum ......................... 494/37 |
| 4,755,300 | 7/1988 | Fischel et al. ..................... 210/650 |
| 4,755,301 | 7/1988 | Bowers ........................... 210/650 |
| 4,770,779 | 9/1988 | Ichikawa et al. ................... 210/516 |
| 4,818,291 | 4/1989 | Iwatsuki et al. .................... 106/124 |
| 4,832,851 | 5/1989 | Bowers et al. ..................... 210/650 |
| 4,874,368 | 10/1989 | Miller et al. ........................ 604/82 |
| 4,879,031 | 11/1989 | Panzani ......................... 210/360.2 |
| 4,902,281 | 2/1990 | Avoy ............................. 604/191 |
| 4,928,603 | 5/1990 | Rose et al. ....................... 106/124 |

(List continued on next page.)

FOREIGN PATENT DOCUMENTS

| | | |
|---|---|---|
| 9103724 | 3/1993 | Brazil . |
| 0 090 997 | 12/1983 | European Pat. Off. . |
| 0 109 374 | 5/1984 | European Pat. Off. . |
| 0 253 198 | 1/1988 | European Pat. Off. . |
| 56103 | 5/1967 | German Dem. Rep. . |
| 42 02 667 | 5/1993 | Germany . |

OTHER PUBLICATIONS

Harris, E.L.V. Concentration of the Extract. In, Protein Purification Methods: A Practical Approach Harris, E. L. V.; Angal, S.; Editors. (1989) Publisher: (IRL Press, Oxford, UK), pp. 67–69.

The American Surgeon, vol. 55, pp. 166–168, Mar. 1989, William D. Spotnitz, MD, et al., "Successful Use of Fibrin Glue During 2 Years of Surgery at a University Medical Center".

Biopolymers, vol. 27, pp. 763–774, 1988, Gerard Marx, "Mechanism of Fibrin Coagulation Based on Selective, Cation–Driven, Protofibril Association".

Ann Thorac Surg, vol. 56, pp. 387–389, 1993, Robert L. Quigley, MD, et al., "Intraoperative Procurement of Autologous Fibrin Glue".

Laryngoscope, vol. 96, pp. 1062–1064, Oct. 1986, Karl H. Siedentop, MD, et al., "Extended Experimental and Preliminary Surgical Findings With Autologous Fibrin Tissue Adhesive Made From Patient's Own Blood".

Laryngoscope, vol. 99, pp. 974–976, Sep. 1989, Kyosti Laitakari, MD, et al., "Autologous and Homologous Fibrinogen Sealants: Adhesive Strength".

Laryngoscope, vol. 95, pp. 1074–1076, Sep. 1985, Karl H. Siedentop, MD, et al., Autologous Fibrin Tissue Adhesive.

Transfusion, vol. 30, No. 8, pp. 741–747, 1990, J.W. Gibble, et al., "Fibrin Glue: The Perfect Operative Sealant?".

Journal of Biomaterials Applications, vol. 7, pp. 309–353, Apr. 1993, David H. Sierra, "Fibrin Sealant Adhesive Systems: A Review of their Chemistry, Material Properties and Clinical Applications".

*Primary Examiner*—Elizabeth C. Kemmerer
*Assistant Examiner*—David S. Romeo
*Attorney, Agent, or Firm*—William B. Walker

[57] ABSTRACT

An inexpensive device with a disposable cartridge for preparing tissue sealant is disclosed. The device is particularly applicable to stat preparation of autologous tissue sealant. A method of sealing tissue in which the tissue sealant is applied immediately after mixing platelet-rich plasma concentrate (from the device) with a solution of calcium and thrombin is also disclosed. Preparation in the operating room of 5 cc sealant from 50 cc patient blood requires less than 15 minutes and only one simple operator step. There is no risk of tracking error because processing can be done in the operating room. Chemicals added may be limited to anticoagulant (e.g., citrate) and calcium chloride. The disposable cartridge may fit in the palm of the hand and is hermetically sealed to eliminate possible exposure to patient blood and ensure sterility. Adhesive and tensile strengths are comparable or superior to pooled blood fibrin sealants made with precipitation methods. Antifibrinolytic agents (such as aprotinin) are not necessary because the tissue sealant contains high concentrations of natural inhibitors of fibrinolysis from the patient's blood. The tissue sealant also contains patient platelets and additional factors not present in available fibrin sealants that promote wound healing.

3 Claims, 4 Drawing Sheets

U.S. PATENT DOCUMENTS

| | | | |
|---|---|---|---|
| 4,943,273 | 7/1990 | Pages | 494/41 |
| 4,957,638 | 9/1990 | Smith | 210/782 |
| 4,983,158 | 1/1991 | Headley | 494/41 |
| 4,985,153 | 1/1991 | Kuroda et al. | 210/782 |
| 5,000,970 | 3/1991 | Shanbhag et al. | 426/296 |
| 5,002,571 | 3/1991 | O'Donnell, Jr. | 623/6 |
| 5,030,215 | 7/1991 | Morse et al. | 604/410 |
| 5,071,570 | 12/1991 | Shiraki et al. | 210/774 |
| 5,100,564 | 3/1992 | Pall et al. | 210/782 |
| 5,112,484 | 5/1992 | Zuk, Jr. | 21/247 |
| 5,137,832 | 8/1992 | Levine et al. | 436/69 |
| 5,141,645 | 8/1992 | Shiraki et al. | 210/513 |
| 5,152,905 | 10/1992 | Pall et al. | 210/767 |
| 5,156,613 | 10/1992 | Sawyer | 606/213 |
| 5,281,342 | 1/1994 | Biesel et al. | 210/782 |
| 5,290,918 | 3/1994 | Bui-Khac | 530/381 |
| 5,298,171 | 3/1994 | Biesel | 210/782 |
| 5,321,126 | 6/1994 | van Dommelen et al. | 530/382 |
| 5,322,620 | 6/1994 | Brown et al. | 210/85 |
| 5,330,974 | 7/1994 | Pines et al. | 514/21 |
| 5,370,802 | 12/1994 | Brown | 210/782 |
| 5,376,263 | 12/1994 | Fischel | 210/87 |
| 5,395,923 | 3/1995 | Bui-Khac et al. | 530/381 |
| 5,403,272 | 4/1995 | Deniega et al. | 604/4 |
| 5,411,885 | 5/1995 | Marx | 435/240.2 |
| 5,420,250 | 5/1995 | Lontz | 530/381 |
| 5,443,481 | 8/1995 | Lee | 606/213 |
| 5,456,693 | 10/1995 | Conston et al. | 606/192 |
| 5,510,102 | 4/1996 | Cochrum | 424/78.08 |

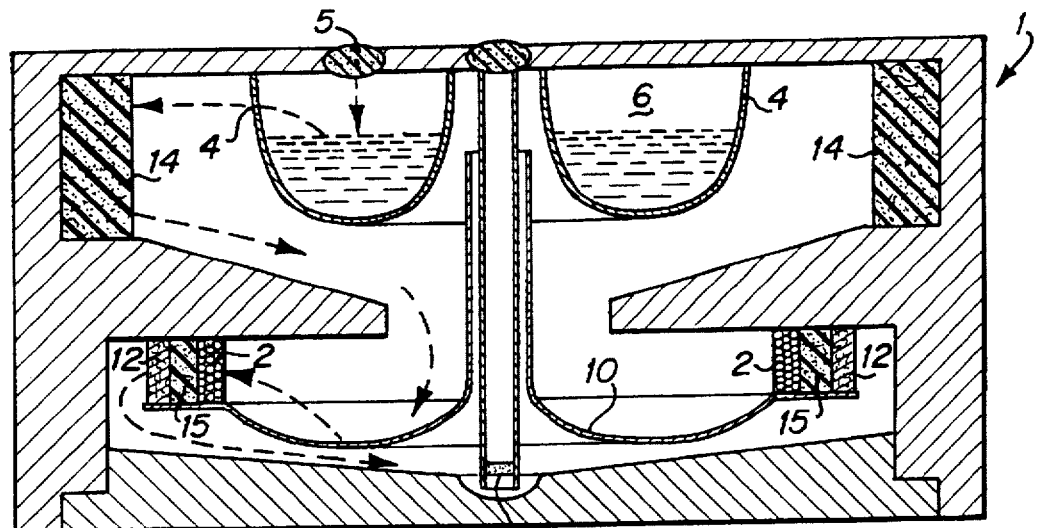
Fig_1
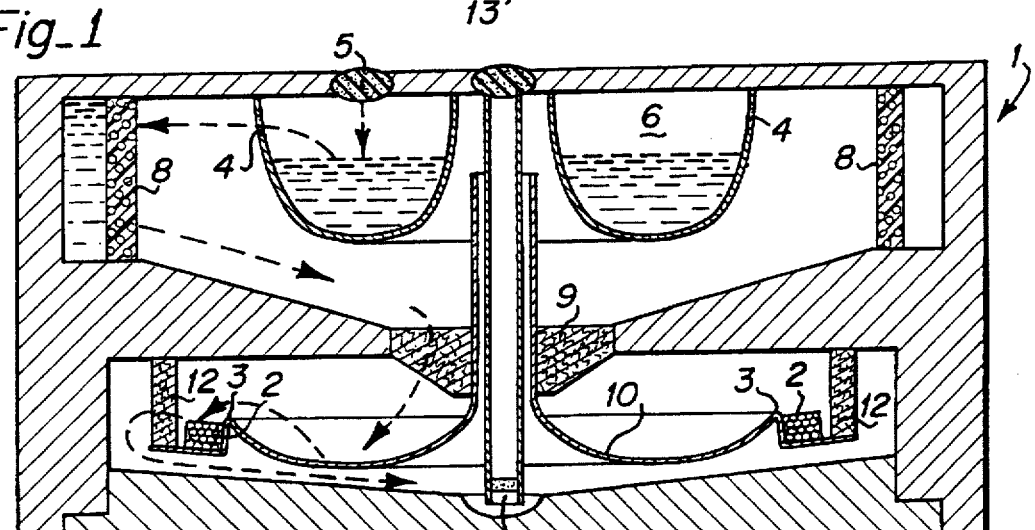
Fig_2
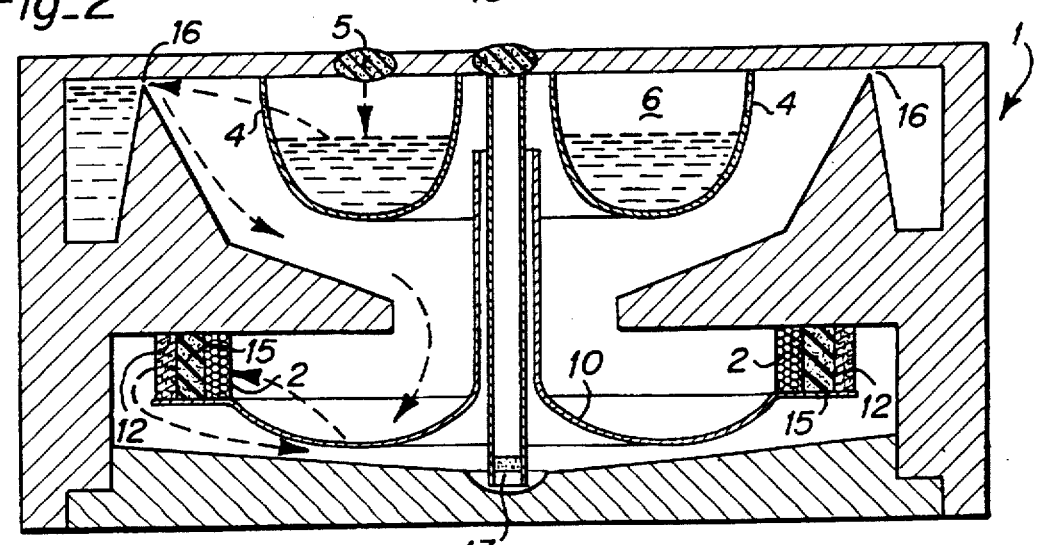
Fig_3

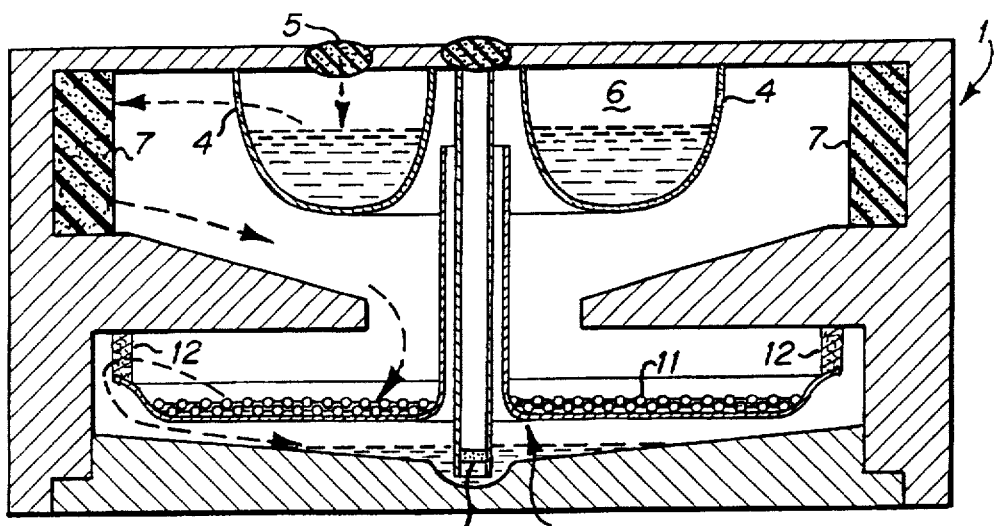
Fig_4
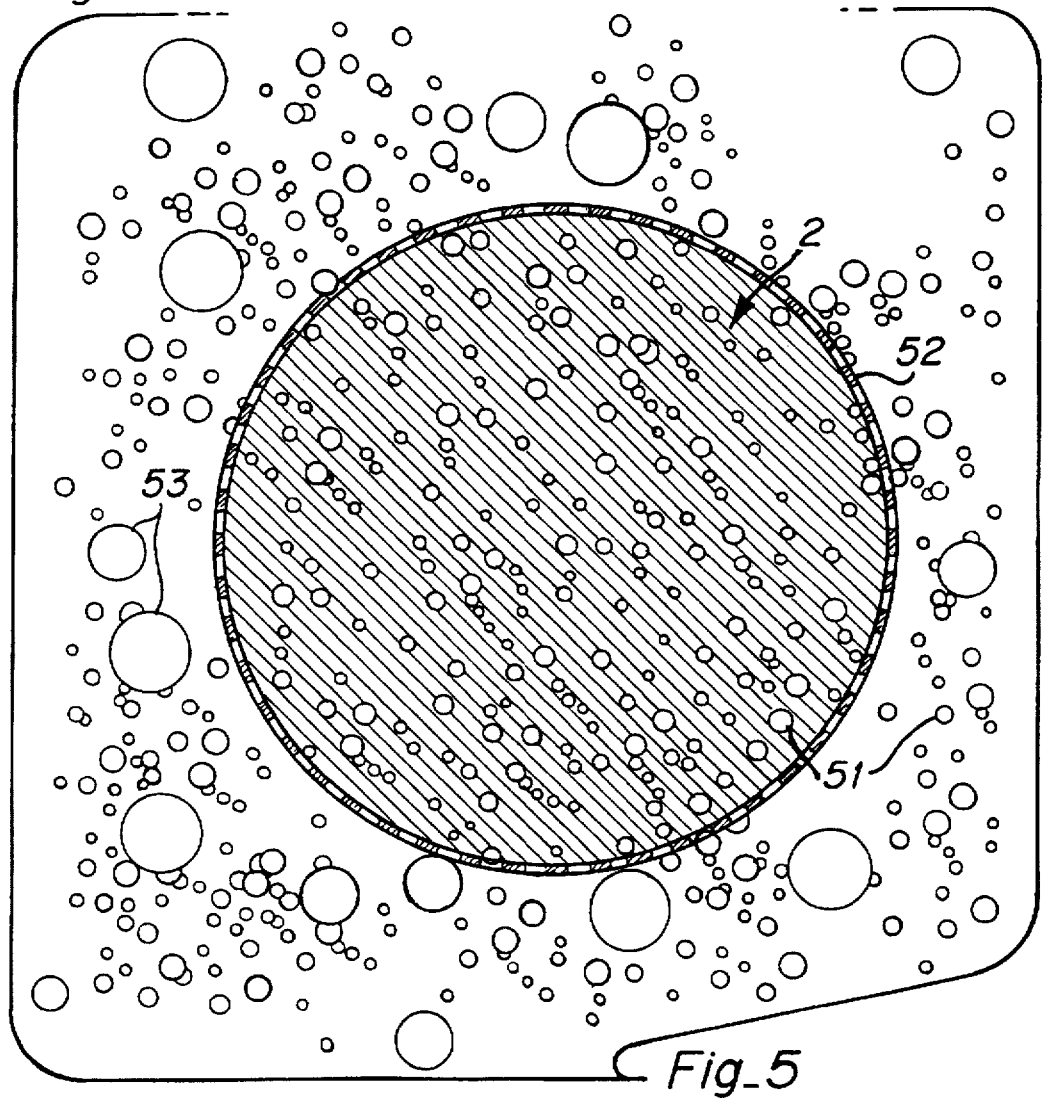
Fig_5

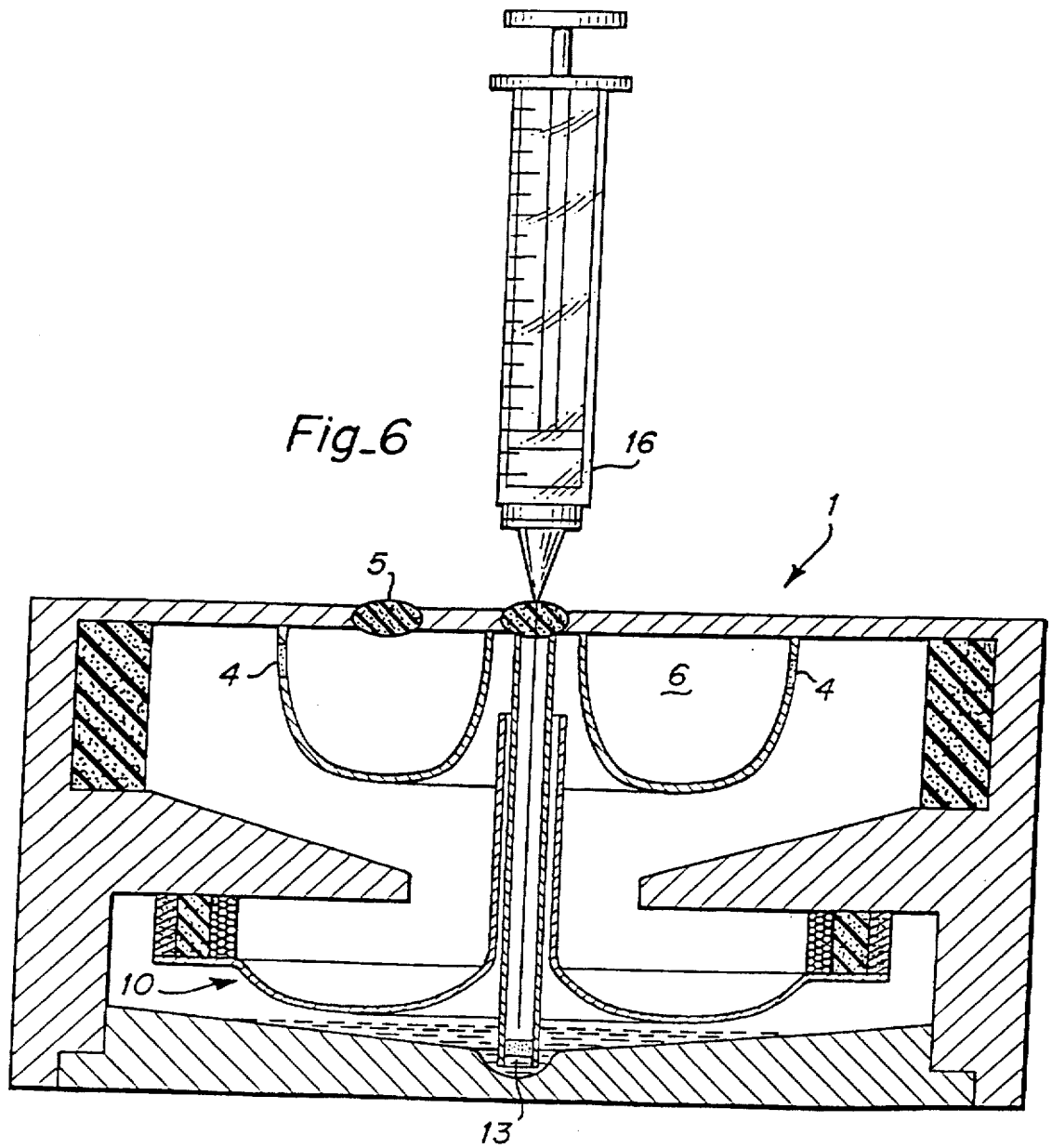
Fig_6

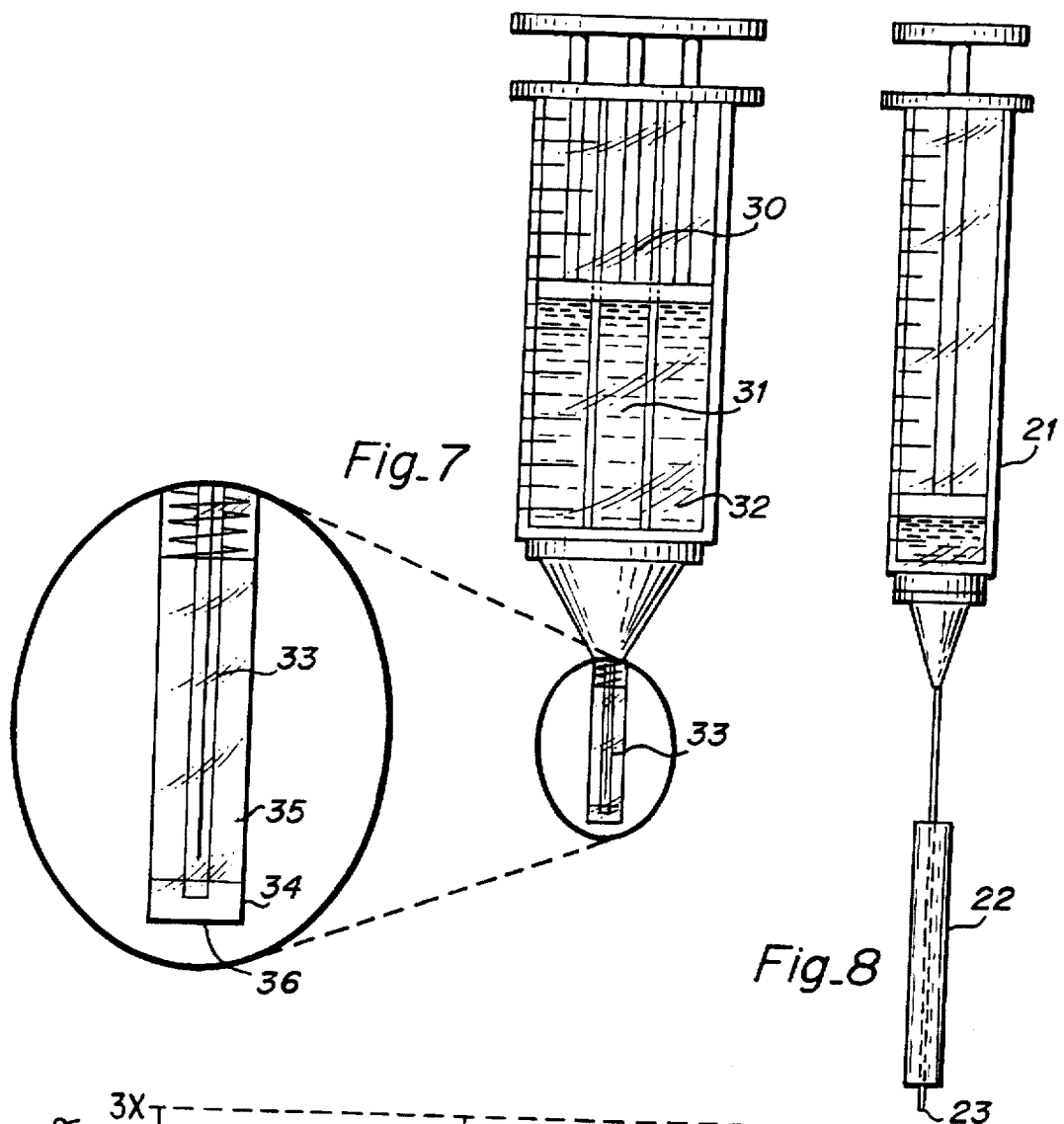
Fig. 7
Fig. 8
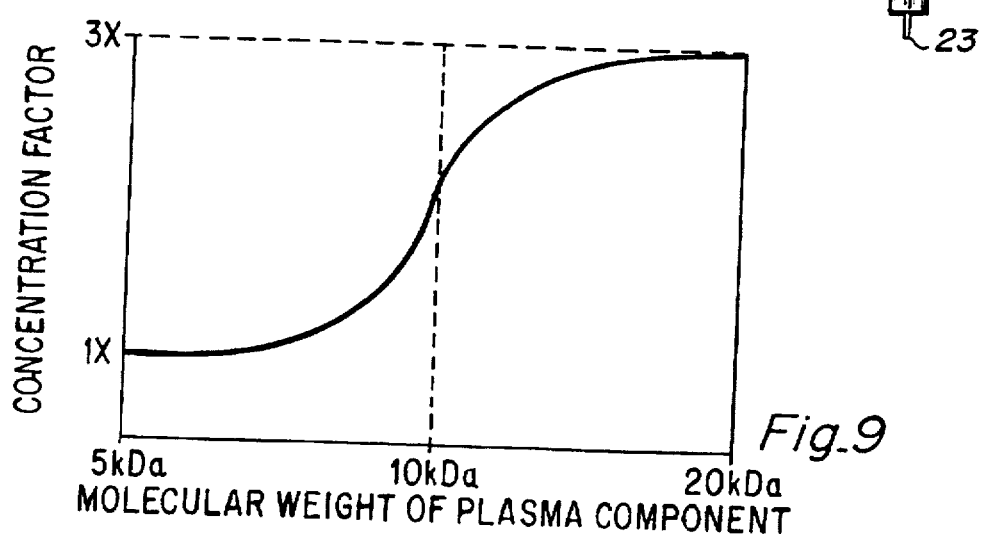
Fig. 9

METHODS FOR MAKING CONCENTRATED PLASMA AND/OR TISSUE SEALANT

This application is a continuation of application Ser. No. 08/351,010 filed Dec. 7, 1944 now U.S. Pat. No. 5,825,008.

BACKGROUND OF THE INVENTION

1. Field of the Invention

The present invention concerns compositions, methods and apparatuses for making concentrated plasma and tissue sealant, for sealing tissue, for rapid separation of higher molecular weight components in mixtures, for rapid separation of blood plasma and for rapid separation of particulate components in mixtures. The present invention is particularly applicable to preparation and use of autologous tissue sealant.

2. Discussion of the Background

Fibrin Glues and Sealants

Various substances have been tried to meet the need for a suitable tissue adhesive for use in surgical procedures. Completely synthetic materials such as cyanoacrylate have been tried and been found wanting. Natural fibrin glues and sealants made from blood components were recognized early in the development of this technology. Surgical "fibrin sealants" (sometimes called "fibrin glues") made up of human fibrinogen activated by bovine thrombin are used extensively in Europe. Such fibrin sealants have been shown to be superior to synthetic adhesives or traditional surgery in many situations. In addition they reduce the need for blood transfusions. Academic and surgical opinion on fibrin sealants is very favorable. A recent review says:

Fibrin sealants are the most successful tissue adhesives to date. They have many advantages over adhesive technologies such as cyanoacrylates and marine adhesives in terms of biocompatibility, biodegradation and hemostasis. There are several commercial products in Europe but none in the United States due to the current regulatory stance against pooled plasma blood products (Sierra, 1993; vide infra).

In current practice, fibrin sealant is made by isolating a concentrate of human fibrinogen, fibronectin and factor XIII, usually by cryoprecipitation, and combining it immediately before use with bovine (or sometimes human) thrombin. The thrombin converts the fibrinogen to fibrin which rapidly gels to form a transient hemostatic plug, which is then stabilized by factor XIII. Fibronectin provides adhesion for cells repopulating the clot and tissue. The most common method of application of fibrin sealant is mixing of concentrated fibrinogen from pooled human blood with bovine thrombin and calcium immediately before use.

Fibrin sealant is not available in the U.S. commercially, but is in Europe (TISSEEL®, TISSUCOL®/Immuno; BERIPLAST®/Behring). Many papers have been published on its use.

Use of fibrin sealant in the United States is limited to preparation within the clinic outside FDA control. The reasons for FDA reluctance to approve these products in the United States are:

- virus transmission (e.g., HIV, hepatitis) from pooled human blood[1] and
- immunological reactions to bovine thrombin[2], for example thrombin and factor V inhibitors or foreign body reactions[3].

These FDA concerns are so serious that the FDA has not approved any fibrin sealant product, despite strong interest from surgeons and very favorable comparative studies in the literature.

These circumstances have led to much attention being given to methods to isolate an autologous counterpart of the fibrinogen containing component in the TISSUCOL system in a practical manner. These efforts are discussed in the reviews cited below. The following from a review by Thompson[4] shows that the value of stat autologous fibrinogen is much anticipated: Fibrin glue is composed of two separate solutions of fibrinogen and thrombin. When mixed together, these agents mimic the last stages of the clotting cascade to form a fibrin clot. Fibrin glue is available in Europe but is not commercially available in the U.S.; therefore, investigators have extemporaneously compounded their own fibrin glue. Fibrinogen can be obtained from pooled, single-donor, and autologous blood donors and is usually isolated by the process of cryoprecipitation . . . The safest preparations use the patient's own blood to prepare fibrin glue . . . Use of . . . autologous blood results in minimal risk of disease transmission, but it requires anticipated use as in an elective procedure. The use of autologous blood usually is not possible in trauma or an emergency surgical procedure.

Siedentop[5] describes a number of approaches to the precipitation of fibrinogen from plasma in the context of the proposed use of this material as the fibrinogen furnishing component of a fibrin glue. Four methods were suggested: precipitation with ethanol, use of unfractionated plasma, cryoprecipitation, and precipitation with ammonium sulfate. Epstein[6] suggests the use of a fibrinogen preparation from autologous plasma obtained using polyethylene glycol precipitation. A system for preparing autologous tissue adhesive using a relatively complex system based on ethanol precipitation has been described by Weis-Fogh[7]. Because none of these methods has yet produced a clearly superior autologous sealant, research in the past five years has continued on several approaches including plasma sealant[8], ethanol precipitation[9] and rapid cryoprecipitation[10]. Prior patents are discussed in later sections, Autologous Precipitate Sealants and Autologous Plasma Sealants.

None of these methods is readily adaptable for convenient use of an autologous plasma fraction as an adhesive which can be prepared quickly during the surgical procedure. All of the approaches suggested for preparation of the fibrinogen containing fraction for this purpose are too time-consuming and complex to be finished in a short enough time to be accomplished during the surgery. Also, in some procedures, such as cryoprecipitation, special equipment, such as refrigerated centrifuges, is required. While the prior art approach is to prepare the composition in advance, this immediately imposes the necessity for additional procedures for identification and retrieval of the samples matched with the patient, and the concomitant opportunity for error, besides the inconvenience to the patient, who must then arrange time for an additional medical appointment. And, of course, this practice is not possible when the surgery is conducted on an emergency basis.

Several useful reviews on surgical glues generally and on fibrin glues particularly have been published (Sierra, D. H. "Fibrin sealant adhesive systems: a review of their chemistry, material properties and clinical applications." *J Biomater Appl7*(4 1993): 309–52; Wiseman, David M., David T. Rovee, and Oscar M. Alverez. "Wound Dressings: Design and Use." In *Wound Healing: Biochemical & Clinical Aspects*, ed. I. Kelman Cohen, Robert F. Diegelmann, and William J. Lindblad. 562–580. 1st ed., Vol. Philadelphia: W. B. Saunders Company, 1992). A review of devices used by surgeons discusses fibrin glue in context of both hemostatic agents and adhesive agents (Edlich, Richard F., George T. Rodeheaver, and John G. Thacker. "Surgical Devices in Wound Healing Management." In *Wound Healing: Biochemical & Clinical Aspects,* ed. I. Kelman Cohen, Robert F. Diegelmann, and William J. Lindblad. 581–600. 1st ed., Vol. Philadelphia: W. B. Saunders Company, 1992). A review of the role of fibrin and fibrinogen in blood coagulation has also been published (Jackson, C. M. and Y. Nemerson. "Blood coagulation." *Annu Rev Biochem*49 (811 1980): 765–811). Other reviews, in reverse chronological order, include:

(1) Lerner, R. and N. S. Binur. "Current status of surgical adhesives." *J Surg Res*48 (2 1990): 165–81.

(2) Gibble, J. W. and P. M. Ness. "Fibrin glue: the perfect operative sealant?" *Transfusion*30 (8 1990): 741–7.

(3) Thompson, D. F., N. A. Letassy, and G. D. Thompson. "Fibrin glue: a review of its preparation, efficacy, and adverse effects as a topical hemostat." *Drug Intell Clin Pharm*22 (12 1988): 946–52.

Biological Precipitate Sealants

The vast majority of prior methods for preparing blood derived glues or sealants use fibrinogen precipitated (usually cryoprecipitated) from pooled plasma, a method first published in 1972[11]. Most biological sealant patents are improvements on cryoprecipitation. Most go through a lyophilization step before application. A few touch on plasma, but none mentions a composition derived from concentrated plasma.

A composition from cryoprecipitation method was patented by Immuno AG[12]. Since the basic method had been published previously, the composition claims were precisely descriptive:

Exemplary Claim: 1. A lyophilized tissue adhesive of mammalian protein origin which comprises fibrinogen, albumin, factor XIII, cold-insoluble globulin and plasminogen-activator inhibitor or plasmin inhibitor wherein the fibrinogen is present in at least 33% by weight, the ratio of factor XIII to fibrinogen, expressed in units of factor XIII per gram of fibrinogen is at least 80; and fibrinogen and albumin are present in a ratio of 33 to 90:5 to 40.

Several inventions have improved on early cryoprecipitation methods. A variation of cryoprecipitation is claimed to produce material superior for patients with blood coagulation disorders[13]. Stroetmann overcame problems by mixing fibrinogen, thrombin and protease inhibitor in lyophilized form for administration as a powder[14]. Behring found a way to improve solubility of (poorly soluble) cryoprecipitate[15]. French scientists have improved the traditional cryoprecipitation by using a double cold ethanol precipitation[16]. Epstein has a patent application for precipitation with polyethylene glycol (only the sister (device) patent has issued)[17]. Cryolife has crafted a patent with a broad exemplary claim[18] (quoted in note), but all the claims are limited by use of a precipitation step.

Sierra's group has patented compositions with collagen added to fibrinogen. The notion is that collagen improves the mechanical properties of the sealant[19]. Related approaches are addition of hyaluronic acid to make the solution more viscous before gelation (patent application)[20] and addition of silk fibroin for mechanical strength[21].

A disclosed World patent application shows that Baxter is using fibrinogen affinity chromatography to get around the problems with precipitation[22]. A disclosed European patent application shows that Squibb scientists have developed a method eliminating the need for thrombin[23]. They use fibrin made by passing fibrinogen through a column with immobilized snake-venom; chaotropic agents prevent gelation. According to this work, "(f)ibrin I monomer is preferred because it can, in contrast to fibrinogen, readily be converted to fibrin polymer without the use of thrombin or factor XIII." From blood, the method yields 60–90% fibrin monomer. It is activated by calcium and a pH change.

The majority of biological patents assume a precipitation step in the manufacture of the tissue sealant.

Autologous Precipitate Sealants

As discussed above, it is widely recognized that autologous blood products are superior for safety and biocompatibility reasons alone. Columbia University has patented the use of autologous fibrin glue[24], but the claims are restricted to cryoprecipitate. A European patent application makes similar claims[25], but again the claims are restricted to cryoprecipitate.

Autologous Plasma Sealants

Alterbaum has patented using small quantities of patient plasma to make tissue glue[26], but the plasma is not concentrated and the claims are restricted to use of flat pack centrifugation for isolation of the plasma.

1. A method for use in the autologous preparation of fibrin glue wherein a patient's blood is separated in a centrifuge having cylindrical cups pivotally mounted to a rotor to obtain plasma and wherein the plasma is separated in the centrifuge to produce concentrated fibrinogen, comprising the steps of: (a) transferring the blood or plasma into a substantially flat packet; (b) fixing the packet containing the blood or plasma in a recess of a substantially cylindrical insert fixture assembly; (c) inserting said cylindrical-shaped insert fixture assembly in a cup of the centrifuge having a complementary cylindrical shape so that the insert fixture assembly is held snugly within said centrifuge cup; (d) centrifuging the blood or plasma contained within said packet fixed in said insert fixture assembly held in said centrifuge cup to separate the blood or plasma into components; and (e) forming fibrin glue from one of said separated components.

Although no claim mentions or suggests concentrating the plasma, the patent which appears to be most similar to the present invention (Dennis Galanakis, SUNY Stony Brook) covers unconcentrated plasma glue[27]:

1. A method of treating with autologous mammalian plasma fibrin to affect hemostasis, comprising the steps of: (a) obtaining a sample of blood from said animal; (b) substantially immediately separating the whole plasma from said blood obtained in step (a); and (c) contacting said whole plasma resulting from step (b) with thrombin in a physiologically acceptable solution at a rate and in a volume at the site of treatment to provide fibrin coagulation at said site.

Applicators

Application of fibrin glue requires mixing the two components under controlled conditions because gelation can be very rapid. The earliest applicator patents are assigned to Immuno AG. The principal claims revolve around different syringe diameters to limit dilution of the fibrinogen component by using a smaller volume of more highly concentrated thrombin[28] and the use of medical gas to keep the syringe applicator/mixer clear of gel[29]. Galanakis described an application in which the two liquids do not mix internally but are applied side-by-side from tubes that run in parallel all the way to the point of application[27]. Very similar claims were made previously by Micromedics[30]. Corus Medical has an aerosol device driven by pressurized gas[31]. The Cryolife approach is to prevent gelation in a single-component fibrin glue by pH inhibition of thrombin[32]. Gordon Epstein has patented the use of a third suction tip to dry the surface before application[17].

Plasma Separators

Haemonetics' "bowl" technology allows separation of plasma continuously by a method which differs from the methods of the present invention disclosed below[33]. Several patents address isolation of platelets from blood using centrifuge sedimentation methods[34] or red cell barriers[35], but none claims an approach similar to the ones described herein including sintered (porous) plastic or in which the cells pass through a barrier, leaving platelet-rich plasma behind.

Dextrans

Pharmacia has basic patents on dextranomers[36] and on their use in wound healing[37]. Interestingly, concentration of proteins (including fibrinogen) in the vicinity of the wound by differential absorption of water and electrolytes is identified as a benefit of the technology, but the claims are limited to methods in which the dextranomer beads are applied to the wound.

Other Patents of Interest

Fibrin sealants have been claimed as a component in a composition to repair cartilage[38], to help in eye surgery[39] and with heat-melted collagen for "tissue welding[40]." Another approach has been to use fibrinogen/thrombin powder to coat a biodegradable fiber to stop puncture bleeding[41], or in a collagen sponge or mat with powdered fibrin sealant[42]. Addition of collagenase to fibrin sealant to improve nerve healing has been patented by Wehling[43]. Pharmacia has patented the use of hyaluronic acid to prevent adhesions[44].

Summary of Current Use of Fibrin Sealants in the United States

Although wounds heal naturally, medicine seeks to improve and speed the wound healing process. The body's blood clotting and tissue repair mechanisms are complex cascades progressing from blood proteins (e.g. fibrinogen) to specialized repair cells (fibroblasts). Sutures, surgical staples or surgical adhesives hold the damaged tissues together so that healing can progress. Surgical "fibrin sealants," sometimes called "fibrin glues," made up of human fibrinogen activated by bovine thrombin are used extensively in Europe. Such fibrin sealants have been shown to be superior to synthetic adhesives or traditional surgery in many situations. In addition they reduce the need for blood transfusions. Academic surgical opinion on fibrin sealants is very favorable (see the reviews cited above).

In current practice, fibrin sealant is made by isolating a concentrate of human fibrinogen, fibronectin and factor XIII, usually by cryoprecipitation, and combining it immediately before use with bovine thrombin. The thrombin converts the fibrinogen to fibrin which then gels rapidly to form a transient hemostatic plug. The most common method of application of fibrin sealant is by mixing of concentrated fibrinogen from pooled human blood with bovine thrombin and calcium immediately before use.

Fibrin sealant is not available in the U.S. commercially, but is in Europe. The FDA is reluctant to approve these products in the United States because of the potential for virus transmission (e.g., HIV, hepatitis) from pooled human blood and the potential for immunological reactions. These FDA concerns are so serious that the FDA has not approved any fibrin sealant product, despite strong interest from surgeons and very favorable comparative studies in the literature.

1. Hennis, H. L., W. C. Stewart, and E. K. Jeter. "Infectious disease risks of fibrin glue [letter]." *Ophthalmic Surg* 23 (9 1992): 640.
2. Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (3 1991): 408–11.
   Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors." *J Thorac Cardiovasc Surg* 105 (5 1993): 892–7.
3. Sanal, M. "Does fibrin glue cause foreign body reactions? [letter]." *Eur J Pediatr Surg* 3 (3 1993): 190. Sanal, M., H. Dogruyol, A. Gurpinar, and O. Yerci. "Does fibrin glue cause foreign body reactions?" *Eur J Pediatr Surg* 2 (5 1992): 285–6.
4. Thompson, D. F., Letassy, N. A., and Thompson, G. D., Fibrin glue: a review of its preparation, efficacy, and adverse effects as a topical hemostat. *Drug Intell Clin Pharm*, 1988. 22 (12): p. 946–52.
5. Siedentop, K. H., D. M. Harris, and B. Sanchez. "Autologous fibrin tissue adhesive." *Laryngoscope* 95 (9 Pt 1 1985): 1074–6.
6. Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40–5.
7. Weis-Fogh, U. S. "Fibrinogen prepared from small blood samples for autologous use in a tissue adhesive system." *Eur Surg Res* 20 (5–6 1988): 381–9.
8. Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992): 357–9.
9. Kjaergard, H. K., Fogh Us Weis, and J. J. Thiis. "Preparation of autologous fibrin glue from pericardial blood." *Ann Thorac Surg* 55 (2 1993): 543–4.
   Kjaergard, H. K., U. S. Weis-Fogh, H. Sorensen, J. Thiis, and I. Rygg. "A simple method of preparation of autologous fibrin glue by means of ethanol." *Surg Gynecol Obstet* 175 (1 1992): 72–3.
10. Casali, B., F. Rodeghiero, A. Tosetto, B. Palmieri, R. Immovilli, C. Ghedini, and P. Rivasi. "Fibrin glue from single-donation autologous plasmapheresis." *Transfusion* 32 (7 1992): 641–3.
    Moretz, W, Jr., J Shea Jr., J. R. Emmett, and J Shea. "A simple autologous fibrinogen glue for otologic surgery." *Otolaryngol Head Neck Surg* 95 (1 1986): 122–4.
11. Matras, Helene, H. P. Dinges, H. Lassmann, and B. Mamoli. "Zur nahtlosen interfaszikularen Nerventransplantation im Tierexperiment." Wein Med Woschtr 122 (37 1972): 517–523.
    First clinical results: Kuderma, H. and Helene Matras. "Die klinische Anwendung der Klebung von Nervenanastomosen mit Gerinnungssubstanzen bei der Rekonstruction verletzter peripherer Nerven." Wein Klin Wochenschr 87 (15 1975): 495–501.
12. Schwarz, O., Linnau, Y., Loblich, F., and Seelich, T., Tissue adhesive; freeze dried wound healing agent containing Fibrinogen, albumin, factor XIII, globulin, and plasminogen blocking Agent. U.S. Pat. No. 4,414,976 (1983); Schwarz, O., Linnau, Y., Loblich, F., and Seelich, T., Tissue adhesive; factor viii, proteins, fibrinogen, globulin, albumin and plasmin inhibitor. U.S. Pat. No. 4,377,572 (1982); Schwarz, O., Linnau, Y., Loblich, F., and Seelich, T., Tissue adhesive; fibrinogen, factor XIII, albumin, plasmin inhibitor. U.S. Pat. No. 4,362,567 (1982); Schwarz, O., Linnau, Y., Loblich, F., and Seelich, T., Tissue adhesive; blood proteins; surgery. U.S. Pat. No. 4,298,598 (1981); assigned to Immuno AG.
13. Martinowitz, U. and Bal, F., Improved tissue glue prepared by using cryoprecipitate. EP (application) Pat. No. 534,178 (1993) Assigned to Octapharma AG.
14. Stroetmann, M., Enriched plasma derivative for advancement of wound closure and healing. U.S. Pat. No. 4,427,650(1984); Stroetmann, M., Fibrinogen-containing dry preparation, manufacture and use thereof. U.S. Pat. No. 4,442,655 (1984); Stroetmann, M., Enriched plasma derivative for enhancement of wound closure and coverage. U.S. Pat. No. 4,427,651 (1984); assigned to Serapharm Michael Stroetmann DE.
15. Fuhge, P., Heimberger, N., Stohr, H.-A., and Burk, W., Readily Dissolvable Lyophilized Fibrinogen Formulation. U.S. Pat. No. 4,650,678 (1987) Assigned to Behringwerke Aktiengesellschaft.
16. Burnouf-Radosevich, M. and Burnouf, T., Concentrate of thrombin coagulable proteins, the method of obtaining same and therapeutical use thereof. U.S. Pat. No. 5,260,420 (1993) Assigned to Centre Regional de Transfusion Sanguine de Lille.
17. Epstein, G. H., Method and apparatus for preparing fibrinogen adhesive from whole blood. U.S. Pat. No. 5,226,877 (1993).
18. Morse, B. S., Carpenter, J. F., Turner, A. D., and Cryolife, I., Preparation of fibrinogen/factor XIII-precipitate. U.S. Pat. No. 5,030,215 (1991) Assigned to Cryolife. Claim 1: A system for collecting a blood coagulation factor comprising a first container means for receiving whole blood, said first container means having an upper end, a lower end, at least one inlet port, add at least one outlet port; first conduit means for conveying whole blood to said first container means, said first conduit means having an end thereof coupled to a said inlet port of said first container means; second container means for receiving plasma which has been separated from red blood cells in said first container means, said second container means having an upper end, the container means having a first, relatively wide diameter portion adjacent to said upper end thereof, a second relatively narrow portion defined below said first portion for receiving a blood coagulation factor precipitate from the plasma within said second container means and a third relatively wide portion defined below said second, relatively narrow portion so that said second, relatively narrow portion defines a relatively narrow passage for precipitate blood coagulation factor from said first portion to said third portion; and second conduit means having a first end thereof coupled to a said outlet port of said first container means and a second end thereof coupled to a said inlet port of said second container means for conveying plasma from said first container means to said second container means.

19. Sierra, D. H., Brown, D. M., and Luck, E. E., Surgical adhesive material. U.S. Pat. No. 5,290,552 (1994) Assigned to Matrix Pharm Inc/Project Hear.
20. Wadstroem, J., Tissue treatment composition comprising fibrin or fibrinogen and biodegradable and biocompatible polymer. WO Pat. No. 92/22,312 (1992).
21. Iwatsuki, M. and Hayashi, T., Silk-fibroin and human-fibrinogen adhesive composition. U.S. Pat. No. 4,818,291 (1989) Assigned to Ajinomoto Co Inc.
22. Tse, D. C., Alpern, M., Enomoto, S. T., Garanchon, C. M., Liu, S. L., Mankarious, S. S., and Thomas, W. R., Topical fibrinogen complex. WO Application Pat. No. 05067 (1993) Assigned to Baxter Int Inc.
23. Edwardson, P. A. D., Fairbrother, J. E., Gardner, R. S., Hollingsbee, D. A., and Cederholm-Williams, S. A., Fibrin sealant compositions and method for utilizing same. EP (Application) Pat. No. 592,242 (1993) Assigned to Squibb.
24. Rose, E. and Dresdale, A., Method of preparing a cryoprecipitated suspension and use thereof. U.S. Pat. No. 4,928,603 (1990) Assigned to Columbia University. Claim 1: A method of preparing a cryoprecipitated suspension containing fibrinogen and Factor XIII useful as a precursor in the preparation of a fibrin glue which consists essentially of: (a) freezing fresh frozen plasma from a single donor which has been screened for blood transmitted diseases at about −80* C.: for at least 6 hours, (b) raising the temperature of the frozen plasma so as to form a supernatant and a cryoprecipitated suspension containing fibrinogen and Factor XIII, and (c) recovering the cryoprecipitated suspension.

Rose, E. and Dresdale, A., Fibrin adhesive prepared as a concentrate from single donor fresh frozen plasma. U.S. Pat. No. 4,627,879 (1986) Assigned to Columbia University. Summary: Prodn. of a fibrin glue comprises preparing a cryoprecipitated suspension contg. fibrinogen and Factor XIII by freezing fresh frozen plasma from a single donor which has been screened for blood transmitted diseases at −80 deg. C. for at least 6 hrs., raising the temp. to form a supernatant and cryoprecipitated suspension contg. fibrinogen and Factor XIII, and recovering the suspension. A defined vol. of the suspension is applied to the desired site and a compsn. contg. thrombin is applied to cause the fibrinogen in the suspension to be converted to the fibrinogen glue, which then solidifies as a gel.
25. Weis-Fogh, U., A Method and an Apparatus for preparing tissue repair promoting substances. WO (Application) Patent No. 88/02259 (1988).
26. Alterbaum, R., Method and apparatus for use in preparation of fibrinogen from a patient's blood. U.S. Pat. No. 4,714,457 (1987). Claim 1: A method for use in the autologous preparation of fibrin glue wherein a patient's blood is separated in a centrifuge having cylindrical cups pivotally mounted to a rotor to obtain plasma and wherein the plasma is separated in the centrifuge to produce concentrated fibrinogen, comprising the steps of: (a) transferring the blood or plasma into a substantially flat packet; (b) fixing the packet containing the blood or plasma in a recess of a substantially cylindrical insert fixture assembly; (c) inserting said cylindrical-shaped insert fixture assembly in a cup of the centrifuge having a complementary cylindrical shape so that the insert fixture assembly is held snugly within said centrifuge cup; (d) centrifuging the blood or plasma contained within said packet fixed in said insert fixture assembly held in said centrifuge cup to separate the blood or plasma into components; and (e) forming fibrin glue from one of said separated components.

27. Galanakis, D. K., Method of preparing autologous plasma fibrin and application apparatus therefore. U.S. Pat. No. 5,185,001 (1993) Assigned to Univ New York State Res Found.
28. Eibl, J., Habison, G., Redl, H., and Seelich, T., Arrangement for applying a tissue adhesive. U.S. Pat. No. 4,735,616 (1988) Assigned to Immuno AG.
29. Redl, H. and Habison, G., Apparatus for Applying a tissue adhesive. U.S. Pat. No. 4,631,055 (1986) Assigned to Immuno AG.
30. Miller, C. H., Altshuler, J. H., and Arenberg, L. K., Fibrin glue delivery system. U.S. Pat. No. 4,874,368 (1989) Assigned to Micromedics.
31. Avoy, D. R., Fibrinogen dispensing kit. U.S. Pat. No. 4,902,281 (1990) Assigned to Corus Med Corp.
32. Morse, B. S., McNally, R. T., and Turner, A. D., Fibrin sealant delivery method. U.S. Pat. No. 5,219,328 (1993) Assigned to Cryolife.
33. Headley, T. D., Plasmapheresis centrifuge bowl; disposable. U.S. Pat. No. 4,983,158 (1991) Assigned to Haemonetics Corp; Pages, E., Disposable centrifuge bowl for blood processing. U.S. Pat. No. 4,943,273 (1990); Latham, A., Jr., Apparatus for separating blood into components thereof. U.S. Pat. No. 4,303,193 (1981); Latham, A., Jr., Process for pheresis procedure and disposable plasma. U.S. Pat. No. 4,204,537 (1980); Latham, A., Jr., Process for pheresis procedure and disposable pheresis bowl therefor. U.S. Pat. No. 4,059,108 (1977); assigned to Haemonetics.
34. Pall, D. B. and Gsell, T. C., Method for obtaining platelets. U.S. Pat. No. 5,258,126 (1993) Assigned to Pall Corp; Pall, D. B. and Gsell, T. C., Blood collection and processing system. U.S. Pat. No. 5,100,564 (1992) Assigned to Pall Corp.
35. Pall, D. B., Gsell, T. C., Matkovich, V. I., and Bormann, T., System and method for processing biological fluid. U.S. Pat. No. 5,217,627 (1993) Assigned to Pall Corp; Pall, D. B., Gsell, T. C., and Muellers, B. T., Method for processing blood for human transfusion. U.S. Pat. No. 5,152,905 (1992) Assigned to Pall Corp; Eldegheidy, M. M., Automatic liquid component separator. U.S. Pat. No. 4,639,316 (1987) Assigned to Becton Dickinson & Co.
36. Process for the Manufacture of Hydrophilic High Molecular Weight Substances from Dextran Substances. GB Pat. No. 854,715 (1965); Gelotte, E. B. and Soderquist, B. G. F., [Hydroxy compound copolymers dextran-epichlorhydrin] Verfahren zur Herstellung von Substitutionsprodukten von Mischpolymerisaten. DD Pat. No. 56,103 (1965); Beil, W., Hoeppner, A., Wolff, H. J., and Beil, H., [Verfahren zur Herstellung von hochmolecularen hydrophilen Vernetzungsproducten von Polysacchariden oder deren Derivaten oder von Polyvinylalkohol in Form von Gelkoernern] High mol. wt. hydrophilic copolymer of a hydroxy group-contng., non-ionic polymer is obtd. in the form of gel grains by reacting the polymer, in the presence. DE Pat. No. 1,443,359 (1962); assigned to Pharmacia.
37. Rothman, U. S. and Jacobsson, S. A., Method for cleansing fluid discharging skin surfaces, wounds and mucous membranes and means for carrying out the method; dry particles of water-insoluble swellable polymer. U.S. Pat. No. 4,537,767 (1985) Assigned to Pharmacia AB; Rothman, U. S. and Jacobsson, S. A., Method for cleansing fluid discharging skin surfaces, wounds and mucous membranes and means for carrying out the method. U.S. Pat. No. 4,225,580 (1980) Assigned to Pharmacia AB.
38. Hunziker, E. B., Method and compositions for the treatment and repair of defects or lesions in cartilage. U.S. Pat. No. 5,206,023 (1993).
39. Sarfarazi, F., Sarfarazi method of closing a corneal incision. U.S. Pat. No. 5,190,057 (1993); O'Donnell, F., E., Jr., Mammen, E., and Nalbandian, R. M., Intraocular lens implant and method of locating and adhering within the posterior chamber. U.S. Pat. No. 5,002,571 (1991).
40. Sawyer, P. N., Collagen welding rod material for use in tissue welding. U.S. Pat. No. 5,156,613 (1992) Assigned to Interface Biomedical Laboratories.
41. Sakamoto, I., Unigame, T., and Takagi, K., Hemostatic agent. U.S. Pat. No. 4,655,211 (1987) Assigned to Unitika KK.
42. Zimmermann, E. and Schiele, U., Agent for sealing and healing wounds. U.S. Pat. No. 4,453,939 (1984) Assigned to Hormon-Chemie Munch; Stemberger, A., Gewebeverklebarre kollagene Wundauflage. EP Pat. No. 102,773 (1983) Assigned to Dr. Ruhland Nachf. GmbH.
43. Wehling, P., Method of enhancing the regeneration of injured nerves and adhesive pharmaceutical formulation therefor. U.S. Pat. No. 5,279,825 (1994) Assigned to Advanced Biofactures; Wehling, P., Method of enhancing the regeneration of injured nerves and adhesive pharmaceutical formulation therefor; supplying collagenase to the zone of nerve injury during regeneration. U.S. Pat. No. 5,173,295 (1992) Assigned to Advanced Biofactures.
44. Lindblad, G. and Buckley, P., Composition and method for prevention of adhesions between body tissues. U.S. Pat. No. 5,190,759 (1993) Assigned to Kabi Pharmacia AB.

SUMMARY OF THE INVENTION

Accordingly, one object of the present invention is to provide a novel method and apparatus for rapidly preparing a plasma concentrate from blood containing fibrinogen, prothrombin (the inactive precursor of thrombin) and other blood proteins, and platelets (thrombocytes) (citrate, heparin or other anticoagulant may be present in an amount sufficient to prevent initiation of clotting).

A further object of the present invention is to provide a novel method and apparatus for rapidly preparing a plasma concentrate from a patient's own blood (autologous tissue sealant).

A further object of the present invention is to provide a novel method and apparatus for rapidly preparing a concentrate from a patient's own blood while in the operating room (stat autologous tissue sealant).

A further object of the present invention is to provide a composition with physical, chemical and biological properties superior to plasma protein precipitate derived tissue sealants.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows an embodiment of a disposable cartridge in accordance with the present invention, employing plasma separation by open cell hydrophobic foam and plasma concentration by open cell foam with beads held thereto by electrostatic force;

FIG. 2 shows an embodiment of a disposable cartridge in accordance with the present invention, employing plasma separation by sintered plastic barrier and plasma concentration by beads distributed in a trough;

FIG. 3 shows an embodiment of a disposable cartridge in accordance with the present invention, employing plasma separation by annular chamber and plasma concentration by open cell foam with beads held thereto by electrostatic force;

FIG. 4 shows an embodiment of a disposable cartridge in accordance with the present invention, employing plasma separation by felt mat and plasma concentration by beads impregnated into plastic discs;

FIG. 5 depicts a single enlarged concentrator bead in a solution of low molecular weight and macromolecule components (e.g., plasma) in accordance with the present invention; and FIG. 6 shows an embodiment of a disposable cartridge in accordance with the present invention after centrifugation and during syringe withdrawal of the plasma concentrate;

FIG. 7 shows an embodiment of the applicator in accordance with the present invention employing coaxial needles to allow mixing of the two components;

FIG. 8 shows an embodiment of the applicator in accordance with the present invention employing an activator cartridge to allow application of single component fibrin sealant; and FIG. 9 graphically shows the relationship between the concentration of proteins and their molecular weight, for a protein solution or suspension concentrated 3X with beads having a molecular weight cutoff of 10 kDa in accordance with the present invention.

DESCRIPTION OF THE PREFERRED EMBODIMENTS

An inexpensive device with a disposable cartridge for preparation of tissue sealant is disclosed. The device is particularly applicable to stat preparation of autologous tissue sealant. The disposable cartridge may fit in the palm of the hand and is hermetically sealed to eliminate possible exposure to patient blood and ensure sterility. Methods of sealing tissue in which the tissue sealant is applied immediately after mixing platelet-rich plasma concentrate (from the device) with a solution of calcium and thrombin or in which the tissue sealant is applied immediately after physical or immobilized enzyme activation are disclosed.

Preparation in the operating room of 5 cc sealant from 50 cc patient blood requires less than 15 minutes and only one simple operator step. There is no risk of tracking error because processing can be done in the operating room. Additional chemicals used in the plasma sealant and preparation thereof may be limited to anticoagulant (for example, citrate) and calcium salts (e.g., chloride).

Adhesive and tensile strengths are comparable to pooled blood fibrin sealants that are available in Europe commercially. Antifibrinolytic agents (such as aprotinin) are not necessary because the tissue sealant contains high concentrations of natural inhibitors of fibrinolysis from the patient's blood. The tissue sealant also contains patient platelets and additional factors not present in available fibrin sealants that promote wound healing.

The present (autologous) tissue sealant gels rapidly as it is mixed with calcium (and optionally bovine or human thrombin) while being applied to the wound. This sealant contains only FDA-approved or approvable components. In the present invention, a "tissue sealant" contains the components found in blood that contribute to clot formation, tissue adhesion and wound healing (preferably all such components in blood), and thus, is distinguished from prior "fibrin sealants" which typically contain only cryoprecipitated proteins and no platelets.

The present invention concerns a method of making platelet-rich plasma (PRP) concentrate, which can then be combined with calcium/thrombin to make tissue sealant. The resulting gel is a composition that has never before been described in the scientific or patent literature.

Referring now to the drawings, wherein like reference numerals designate identical or corresponding parts throughout the several views, and more particularly to FIG. 1 thereof, in a preferred embodiment of the present invention, citrated plasma is processed in two stages in a disposable centrifuge cartridge. In a first stage, platelet-rich plasma is separated from cells when centrifugal force causes red and white cells to lodge irreversibly in a first separator (e.g., a hydrophobic open cell foam). In a second stage, the platelet-rich plasma is concentrated by contact with a concentrator (e.g., dextranomer beads) that absorbs water, electrolytes and small proteins, leaving a platelet-rich plasma concentrate. Thus, the present method of making platelet-rich plasma comprises the steps of:

(a) separating plasma and platelets from whole blood;

(b) contacting the plasma and platelets with a concentrator to provide the concentrated platelet-rich plasma; and (c) separating the concentrated platelet-rich plasma from the concentrator.

Preferably, the cartridge is disposable and sealed (e.g., see housing 1 in each of FIGS. 1 through 4), making contamination impossible. Where the method is performed in a sealed cartridge, the separating step (a) above may be conducted, for example, in a first chamber of the cartridge which is in fluid communication with the blood fill port (inlet). The plasma and platelets may then be contacted with a concentrator (e.g., in a second chamber of the cartridge in fluid communication with the first chamber) sufficiently to concentrate the plasma. An advantage of the sealed, disposable cartridge is that it can be used in the operating room, thus eliminating the possibility of tracking errors and contamination.

In a further embodiment, the method is one for making autologous concentrated platelet-rich plasma, in which the method above for making concentrated platelet-rich plasma further comprises, prior to the separating step (a), collecting blood from a patient and adding an effective mount of citrate to inhibit coagulation (in accordance with standard methods), and injecting a standard quantity of blood (e.g., 50 cc) into the blood fill port (inlet) 5 of a cartridge 1.

Plasma is separated from blood by a combination of conventional centrifugation technology and inventions for ease of separation of the packed cells from the plasma. Centrifuges which are capable of spinning at variable speeds up to 3,000–10,000 rpm in either direction and which are capable of being controlled by a microprocessor (i.e., for spinning at predetermined rates of rotation for predetermined lengths of time) are known and are easily adapted, if necessary, for use with the present apparatus for separating and concentrating plasma. Following injection of the whole blood, the operator starts the microprocessor-controlled centrifuge by push-button. All remaining steps until removal of the concentrate may be automatic.

Although cells are conventionally separated from plasma by their property of packing into a cell mass during centrifugation (then typically aspirated), the cartridges are designed to effect rapid separation of the plasma into the next, concentrator chamber. In one embodiment (FIG. 1), red and white cells remain trapped in a hydrophobic open cell foam 14. In another embodiment (FIG. 4) red and white cells remain trapped in a felt annulus 7. In a third embodiment (FIG. 2) the cells pass through sinuous pathways in a sintered annulus 8 and remain trapped outside. In a fourth embodiment (FIG. 3) red and white cells migrate through a small gap 16 and remain trapped in an outer annulus by the force of gravity when the centrifuge stops.

Optionally, the plasma may be contacted with dextranomer beads that have been bonded by electrostatic force with an open, hydrophobic cellular foam 15 (in accordance with the apparatus of FIGS. 1 and 3). When wetted the beads lose their electrostatic attraction and begin to swell. Alternatively, the plasma may be contacted with free dextranomer beads 2, e.g., in accordance with the apparatus of FIG. 2. The centrifuge may rotate briefly clockwise then counterclockwise a few times at a speed sufficient to evenly distribute the free dextranomer beads 2 outside the concentrator cup lip 3.

The centrifuge may then spin at from 1,000 to 10,000 rpm, preferably 3,000 rpm, for one to ten minutes to separate platelet-rich plasma from cells. First, the whole blood passes through a pore 4 in the blood inlet 6 into the separation chamber. Cells may become trapped in a matrix 14 (as shown in FIG. 1), enmeshed in a matrix 7 (as shown in FIG. 4), or pass through sintered hydrophobic plastic or other porous material 8 (as shown in FIG. 2), leaving platelet-rich plasma in the chamber.

The centrifuge may then be stopped for 15–90 seconds. Under the force of gravity, the platelet-rich plasma passes through an annulus (or through a hydrophilic filter 9) into the second chamber 10 (the lower chamber in FIGS. 1 through 4). This chamber may also be identified as a first concentrator chamber.

In the first concentrator chamber, platelet-rich plasma comes into contact with the concentrator (e.g., dextranomer or polyacrylamide), either bonded by electrostatic force with an open, hydrophobic cellular foam 15 (FIGS. 1 and 3) or free beads 2 (FIG. 2) or beads embossed onto disc(s) 11 (FIG. 4). Dextranomer and polyacrylamide concentrators are commercially available (as SEPHADEX from Pharmacia and as BIO-GEL P from Bio-Rad Laboratories, respectively). Alternatively, instead of dextranomer or polyacrylamide absorbent beads, other concentrators, such as SEPHADEX moisture or water absorbants (available from Pharmacia), other polyacrylamide absorbants, silica gel, zeolites, dextramines, alginate gel, starch, cross-linked agarose, etc., in the form of beads or discs are also acceptable concentrators.

In essence, any material that absorbs water (i.e., which is sufficiently dry to permit water absorption) and which does not significantly denature the proteins essential to blood clotting (e.g., fibrinogen and factor XIII) can be used as a concentrator, as can appropriately-selected membranes, which may also employ an osmotic gradient. Further, where the centrifuge has autoclavelike capabilities (i.e., the ability to rotate its contents at elevated temperatures and/or atmospheric pressures other than 1 atm), mechanical concentrators, such as an elevated temperature (e.g., a temperature of 30°–80° C., preferably 35°–60° C.) or a reduced pressure/vacuum (e.g., 0.1–500 Torr, preferably 1–200 Torr) may serve as a concentrator. However, beads employed as described both above and hereunder are the preferred concentrator.

To maximize results, initial slow rotation of the centrifuge aids mixing (and thus contact) of the concentrator and the plasma. "Slow rotation" refers to a centrifuge speed of from 20 rpm to 500 rpm, preferably from 100 rpm to 300 rpm.

The porosity and hydrophobicity of the porous wall 7, 8 or 14 are such that the low centrifugal force generated is sufficient to drive plasma up the wall but is not sufficient to overcome surface tension, and the plasma remains with the compartment at the inner surface.

The beads 2 swell with water, ions, and low molecular weight proteins 51 (see FIG. 5). The size of the pores 52 in the concentrator bead 2 is chosen so that the higher molecular weight proteins 53 become concentrated in the space around the beads. Any commercially available bead concentrators for concentrating proteins having a molecular weight above a certain preselected molecular weight cutoff value may be used.

As those of ordinary skill in protein chromatography understand, a "molecular weight cutoff" refers to pores in a matrix (e.g., SEPHADEX) which are distributed about a mean size. Moieties (e.g., proteins) more than, for example, 25–50% smaller than mean size diffuse into the bead rapidly, and moieties more than, for example, 25–50% larger than mean size do not diffuse into the bead. Proteins having a size within, for example, 25–50% of the mean size diffuse into the bead slowly (depending on the particular bead selected). Thus, a bead having a molecular weight cutoff of 10 kDa concentrates proteins according to molecular weight as shown graphically in FIG. 9.

Consequently, in the present application, "high molecular weight compounds" refer to those compounds having a molecular weight greater than the preselected molecular weight cutoff value of the concentrator. Examples of high molecular weight proteins in plasma may include fibrinogen and factor XIII, depending on the selected molecular weight cutoff. Preferred concentrator materials include those beads or materials having a molecular weight cutoff value of 100 kDa, preferably 30 kDa and more preferably 5 kDa.

It is important to note that the platelet-rich plasma concentrate contains all components of the original plasma, in either the original concentration (ions and compounds with molecular weight less than the concentrator cutoff) or at a greater concentration than naturally-occurring plasma (e.g., platelets and compounds with molecular weight more than the concentrator cutoff). The protein concentrate contains the same ion concentrations as the unconcentrated plasma.

The quantity of beads is chosen so that the platelet rich plasma is concentrated by a desired amount, e.g., 3×(the approximate level of concentration achieved by a predetermined volume of fluid surrounding close-packed spheres in the same volume). When using DEBRISAN (trademark, Johnson and Johnson), approximately 2.6 gm is required per 10 cc plasma to achieve 3-fold concentration.

After absorption of water and low molecular weight solutes into the concentrator, the rate of rotation is increased (e.g., to 1,000–10,000 rpm, preferably to about 3,000 rpm), forcing the concentrated platelet-rich plasma out through a filter 12 into an outer compartment. The centrifuge may then be stopped, and under the force of gravity, concentrated platelet-rich plasma may be collected in a bottom well 13. The concentrated platelet-rich plasma may be left for extended periods (e.g., hours) without spontaneous gelation or other deleterious effect.

Concentrated platelet-rich plasma, ready for use, may then be removed into a syringe 16 as in FIG. 6.

Thus, the present invention also concerns a method of sealing tissue, comprising the steps of contacting the present concentrated plasma with an activator (either a thrombin/calcium solution or disrupted platelets as described below) to provide an activated plasma concentrate, and applying the activated plasma concentrate to tissue in need of sealing.

In one embodiment of the method of sealing tissue, a separately-prepared solution containing amounts of thrombin and calcium effective to coagulate the concentrated plasma may be combined with the concentrated plasma (in accordance with methods described in the literature for cryoprecipitated fibrinogen). Once combined, the solution and concentrated plasma rapidly gel to form a tissue sealant. An embodiment with features superior to any previously described is shown in FIG. 7. In the barrel of the syringe a cylindrical chamber 31 containing thrombin and calcium solution is surrounded by an annular chamber 32 containing concentrated platelet-rich plasma. Plunger 30 causes the solutions to exit the apparatus through a coaxial needle, 33 (thrombin) and 35 (concentrated plasma), and mix at the tip 36. An optional sleeve 34 ensures proper mixing, and may be retracted to expose premature gel for easy removal.

In a further optional embodiment, a needle tip designed to activate fibrinogen may be used to apply a single-component concentrate (i.e., the concentrated plasma) without the use of added thrombin. In this embodiment, calcium is added to the concentrate immediately prior to or during its application to tissue in need of sealing. FIG. 8 shows a syringe 21 and applicator needle tip 23 separated by activator cartridge 22 through which platelet-rich plasma passes for activation by immobilized proteolytic enzyme, e.g., bovine thrombin.

In a further optional embodiment, a needle tip designed to disrupt platelets may be used to apply a single-component concentrate (i.e., the concentrated plasma) without the use of thrombin. In this embodiment, calcium is added to the concentrate immediately prior to or during its application to tissue in need of sealing. FIG. 8 shows a syringe 21 and applicator needle tip 23 separated by activator cartridge 22 through which platelet-rich plasma passes for activation by, e.g., nylon wool.

The present invention also concerns an apparatus for concentrating platelet-rich plasma, comprising:
- an inlet,
- a first chamber in fluid communication with the inlet, containing a first separator for separating plasma and platelets from whole blood, thus forming platelet-rich plasma,
- a second chamber in fluid communication with the first chamber, containing a concentrator for concentrating the platelet-rich plasma and a second separator for separating the concentrated platelet-rich plasma from the concentrator, and
- an outlet for withdrawing the concentrated platelet-rich plasma.

In a further embodiment, the first separator comprises an open cell hydrophobic foam which traps red blood cells and white blood cells therein under surface tension force.

In a further embodiment, the first separator comprises a porous plastic wall which allows passage of red blood cells and white blood cells therethrough under a centrifugal force, but does not permit passage of red blood cells and white blood cells in the absence of the centrifugal force.

In a further embodiment, the first separator comprises an annulus at the top of the first chamber that allows red blood cells and white blood cells to pass into an outer annulus and be separated from plasma, maintained by gravity when the centrifuge stops.

In a further embodiment of the apparatus, the concentrator may be embedded onto a paper disc, or onto a plurality of discs (of any commercially available material), or may stick electrostatically or by other forces to an open cell matrix.

Many designs of a preferred embodiment of the present cartridge are envisioned (for example, FIGS. 1 through 4).

The designs of the first and second chambers are largely independent, and may be combined into a single cartridge at will. All four designs shown have at least one separation chamber in fluid connection with at least one concentration chamber.

The most preferred embodiment, FIG. 1, uses open cell hydrophobic foam 14 for separation of plasma from cells and effects plasma concentration by beads held by electrostatic force in an open cell foam 15. Another preferred embodiment, shown in FIG. 2, uses plasma separation by sintered plastic barrier 8 and plasma concentration by beads distributed in a trough 2. Another preferred embodiment, shown in FIG. 3, uses plasma separation by annular chamber 16 and plasma concentration by beads held by electrostatic force within open cell foam 15. Another preferred embodiment, shown in FIG. 4, uses plasma separation by felt mat 7 and plasma concentration by beads impregnated into plastic discs 12.

Each separator can be used with each concentrator. The four separators may be combined with the three concentrators to give twelve possible arrangements for the disposable cartridge.

A. Open Cell Hydrophobic Foam Plasma Separator and Dextranomer Bead in Open Cell Hydrophobic Foam Concentrator In FIG. 1, the ready cartridge is shown in the right half and the path of the liquid is shown by the dashed arrows on the left half. The entire chamber is radially symmetric except the septum 5 for the whole blood inlet. The receiving cup 6 holds blood until centrifugal force causes blood to pass through the filter 4. In the separation chamber, centrifugal force causes cells to pass into the open cell hydrophobic foam 14 and accumulate therein; continuing centrifugal force causes cells to migrate into the annulus of open cell foam and platelet rich plasma to remain within the separation chamber. The open cell hydrophobic foam 14 is a honeycomb-like hydrophobic material which allows fluids and small particles to flow freely (e.g., open cell polyurethane foam). Like a wetted sponge, the foam holds liquid against a certain head of pressure due to surface tension forces. Thus, blood cells or other suspended particulates remain entrapped within the foam when the centrifuge stops and separated platelet-rich plasma drains from the surface under the force of gravity. Foam can be either rigid or flexible and can be formed into the appropriate annular shape for the device by molding or die-cutting. The parts are sized so that the packed cell (e.g., erythrocyte and leukocyte) layer is fully contained within the outer open cell foam chamber, which retains the cells when the centrifuge stops.

Concentration comes about when platelet-rich plasma contacts concentrator (e.g., dextranomer) beads 2 in the concentration chamber 10. These beads may be a molecular sieve used in chromatography (SEPHADEX, available from Pharmacia; BIO-GEL P, available from Bio-Rad Laboratories) and debriding (DEBRISAN, available from J&J), or may comprise silica gel, zeolites, dextramines, alginate gel, starch, cross-linked agarose, etc. DEBRISAN appears similar to SEPHADEX G-25, and both are available commercially.

The beads are held by static electric forces onto the surface of open cell hydrophobic foam 15. The open cell hydrophobic foam 15 is a honeycomb-like hydrophobic material. After the platelet-rich plasma has entered the concentration chamber 10, the cartridge 1 is gently rotated to mix platelet-rich plasma with concentrator beads 2. As the fluid penetrates the open foam 15, the beads lose their affinity for the foam and begin to swell. Foam 15 may be made from the same material as foam 14 (e.g., open cell polyurethane), but may have a different porosity. The porosity of foams 14 and 15 is selected empirically on the basis of the sizes and/or types of particles to be retained (e.g., cells by foam 14 and concentrator beads by foam 15). In commercially available open cell, three-dimensional polyurethane foams, porosity is known to be correlated to density (which is measured in, e.g., weight per cubic foot).

After a few minutes (e.g., 1–10 min., preferably 3–5 min.), the concentration is complete. Note that concentration by approximately three times corresponds to fluid surrounding close-packed spheres; thus, three times concentration is optimal. Concentration of more than three times is possible, but to achieve best results, a second concentration chamber should be used for further concentration of plasma concentrated in a first chamber. Thus, concentration of nine times is possible for a three-chamber cartridge containing two concentration chambers.

When concentration is complete, the centrifuge increases its rate of rotation and the increased centrifugal forces cause concentrated platelet-rich plasma to pass through the hydrophobic annulus 12. Sintered plastic 12 (e.g., POREX) is comprised of small particles of plastic fused to create a porous structure. Fluids and small particulates can flow freely through the tortuous pathways defined by the spaces between the fused plastic particles when the material is wet. If the plastic is not specially formulated or treated, the sintered plastic will be hydrophobic and when in the dry state will afford resistance to influx of water, more greatly as the size of the pathways is reduced. This property of "entry pressure" allows the wetting of the surface of a hydrophobic porous wall without substantial entry of fluid into the material. At greater pressure, i.e., when centrifugal force is increased, this resistive force is overcome and fluid breaks through the barrier to enter and pass through the porous wall.

The centrifuge stops, and concentrated platelet-rich plasma runs to the bottom under the force of gravity and is ready to be removed through filter 13 as in FIG. 6.

Finally, note that the concentrator cup 10 is shaped like an inverted funnel to vent the lower chamber to the upper chamber allowing displacement of air from the lower chamber by plasma.

B. Hydrophobic Porous Wall Plasma Separator and Free Dextranomer Bead Concentrator In FIG. 2, the ready cartridge is shown in the right half and the path of the liquid is shown by the dashed arrows on the left half. The entire chamber is radially symmetric except the septum 5 for the whole blood inlet. The receiving cup 6 holds blood until centrifugal force causes blood to pass through the filter 4. In the separation chamber, centrifugal force causes cells to pass through the sinuous channels of filter 8 and accumulate in the outer annulus. The filter 8 (e.g., 80μ POREX) is comprised of small particles of plastic fused to create a porous structure. Fluids and small particulates can flow freely through the tortuous pathways defined by the spaces between the fused plastic particles when the material is wet. If the plastic is not specially formulated or treated, the sintered plastic will be hydrophobic and when in the dry state will afford resistance to influx of water, more greatly as the size of the pathways is reduced. This property of "entry pressure" allows the wetting of the surface of a hydrophobic porous wall without substantial is entry of fluid into the material. At greater pressure, i.e., when centrifugal force is increased (e.g., at 1000–10,000 rpm or higher), this resistive force is overcome and fluid breaks through the barrier to enter and pass through the porous wall. This leaves plasma and platelets in the chamber. The parts are sized so that the packed cell (e.g., erythrocyte and leukocyte) layer is fully contained within the filter and outer annulus. When the centrifuge stops and the platelet-rich plasma passes through the hydrophilic funnel filter 9, the force of gravity is insufficient to cause cells to pass through the filter 8 and back into the separation chamber.

Hydrophilic funnel filter 9 separates the upper and lower compartments so that the loose beads cannot tumble into the upper compartment during shipping and handling. This material might, for example, be similar to that used for filter 8. In order that entry pressure not be so high as to preclude free drainage of plasma (by gravity) into the lower compartment after separation from blood cells, however, this material would preferably be of effective porosity minimally sufficient to ensure entrapment of beads in the concentrator chamber 10. The material would also most desirably be treated in a manner such as to render it more hydrophilic, (e.g., plasma or corona treated or blended or coated with surfactant) in order to further reduce entry pressure.

Concentration comes about when platelet-rich plasma contacts concentrator beads 2 in the concentration chamber 10. These beads may be a molecular sieve used in chromatography (SEPHADEX, available from Pharmacia; BIO-GEL P, available from Bio-Rad Laboratories) and debriding (DEBRISAN, available from J&J), or may comprise silica gel, zeolites, dextramines, alginate gel, starch, cross-linked agarose, etc. DEBRISAN appears similar to SEPHADEX G-25, and both are available commercially.

The beads are sealed into the chamber, but may become unevenly distributed during shipment. A hydrophilic filter 9 keeps the beads in the concentrator chamber 10. Immediately after the addition of whole blood, the cartridge may be gently rotated and counter-rotated a few times to evenly distribute the beads behind the lip 3.

After the platelet-rich plasma has entered the concentration chamber 10, the cartridge 1 is gently rotated to mix platelet-rich plasma with concentrator beads 2. For best results, it is important to keep the slurry in motion because of the tendency for protein to locally concentrate around each bead, retarding absorption. After a few minutes (e.g., 1–10 min., preferably 3–5 min.), the concentration is complete. Note that concentration by approximately three times corresponds to fluid surrounding close-packed spheres; thus, three times concentration is optimal. Concentration of more than three times is possible, but to achieve best results, a second concentration chamber should be used. Thus, concentration of nine times is possible for a three-chamber cartridge containing two concentration chambers.

When concentration is complete, the centrifuge increases its rate of rotation and the increased centrifugal forces cause concentrated platelet-rich plasma to pass through the hydrophobic annulus. Finally, the centrifuge stops, and concentrated platelet-rich plasma runs to the bottom under the force of gravity and is ready to be removed.

Finally, note that the concentrator cup 10 is shaped like an inverted funnel to vent the lower chamber to the upper chamber allowing displacement of air from the lower chamber by plasma.

C. Annular Chamber Plasma Separator and Dextranomer Bead in Open Cell Hydrophobic Foam Concentrator In FIG. 3, similar to FIG. 1 in many respects, the ready cartridge is shown in the right half and the path of the liquid is shown by the dashed arrows on the left half. The entire chamber is radially symmetric except the septum 5 for the whole blood inlet. The receiving cup 6 holds blood until centrifugal force causes blood to pass through the filter 4. In the separation chamber, centrifugal force causes cells to pass above the lip 16 into an outer annular chamber and accumulate therein; continuing centrifugal force causes cells to migrate into the outer annulus and platelet rich plasma to remain within the separation chamber. The parts are sized so that the packed cell (e.g., erythrocyte and leukocyte) layer is fully contained within the outer annular chamber, which retains the cells when the centrifuge stops. When the centrifuge stops, the platelet-rich plasma flows into the concentrator chamber 10.

Concentration comes about when platelet-rich plasma contacts concentrator beads 2 in the concentration chamber 10. These beads are a molecular sieve used in chromatography (SEPHADEX, available from Pharmacia; BIO-GEL P. available from Bio-Rad Laboratories) and debriding (DEBRISAN, available from J&J), or may comprise silica gel, zeolites, dextramines, alginate gel, starch, cross-linked agarose, etc. DEBRISAN appears similar to SEPHADEX G-25, and both are available commercially.

As in FIG. 1, the beads are held by static electric forces onto the surface of open cell hydrophobic foam 15. The open cell hydrophobic foam 15 is a honeycomb-like hydrophobic material. After the platelet-rich plasma has entered the concentration chamber 10, the cartridge 1 is gently rotated to mix platelet-rich plasma with concentrator (dextranomer) beads 2. As the fluid penetrates the open foam 15, the beads lose their affinity for the foam and begin to swell. For best results, it is important to keep the slurry in motion because of the tendency for protein to locally concentrate around each bead, retarding absorption. After several minutes, the concentration is complete. Note that concentration by approximately three times corresponds to fluid surrounding close-packed spheres; thus, three times concentration is optimal. Concentration of more than three times is possible, but to achieve best results, a second concentration chamber should be used. Thus, concentration of nine times is possible for a three-chamber cartridge containing two concentration chambers.

When concentration is complete, the centrifuge increases its rate of rotation and the increased centrifugal forces cause concentrated platelet-rich plasma to pass through the hydrophobic annulus 12. Sintered plastic 12 is made of POREX, comprised of small particles of plastic fused to create a porous structure. Fluids and small particulates can flow freely through the tortuous pathways defined by the spaces between the fused plastic particles when the material is wet. If the plastic is not specially formulated or treated, the sintered plastic will be hydrophobic and when in the dry state will afford resistance to influx of water, more greatly as the size of the pathways is reduced. This property of "entry pressure" allows the wetting of the surface of a hydrophobic porous wall without substantial entry of fluid into the material. At greater pressure, i.e., when centrifugal force is increased (e.g., at 1000–10,000 rpm or higher), this resistive force is overcome and fluid breaks through the barrier to enter and pass through the porous wall.

The centrifuge stops, and concentrated platelet-rich plasma runs to the bottom and is ready to be removed through filter 13 as in FIG. 6.

Finally, note that the concentrator cup 10 is shaped like an inverted funnel to vent the lower chamber to the upper chamber allowing displacement of air from the lower chamber by plasma.

D. Fibrous Matrix Plasma Separator and Dextranomer-Impregnated Disc Concentrator FIG. 4 is similar to the previous figures in many respects. Like FIG. 1, the ready cartridge is shown in the right half and the path of the liquid by the dashed arrows on the left half. The entire chamber is radially symmetric except the septum 5 (the whole blood inlet).

Separation is done by driving cells into a felt or foam mat 7. The parts are sized so that the packed cell (e.g., erythrocyte and leukocyte) layer is fully contained within the felt or foam filter, which retains the cells when the centrifuge stops.

In this design, even distribution of the dextranomer beads is assured by using plastic discs embossed with dextranomer beads. This can be done either with heat or solvent softening of the plastic followed by dipping in dextranomer beads or affixing beads to the plastic with adhesive. As the beads swell they detach from the discs. Separation of the concentrated platelet-rich plasma is done as in the above description of the present method of making concentrated platelet-rich plasma.

E. Method of Manufacture of the Disposable Cartridge

The various rigid plastic components comprising the cartridge are manufactured by injection molding or by pressure- or vacuum-forming, assembled and sealed by conventional methods (e.g., either by adhesives or welding). From FIGS. 1 through 4 it will be apparent to one skilled in the art of plastics fabrication that manufacture is relatively simple and inexpensive. The final assembled product is packaged, radiation sterilized and ready for distribution.

F. Plasma Concentrate, Platelet-rich plasma Concentrate and Tissue Sealant

The present invention also concerns a plasma concentrate, prepared by the present process. The present plasma concentrate may be platelet-rich, platelet-poor or platelet-free (i.e., the platelet concentration is not limited), but is preferably platelet-rich. The concentration of platelets can be controlled by the sedimentation rate, in accordance with known procedures and/or known platelet sedimentation behavior. Preferably, the plasma concentrate is autologous (administered to the patient from whom the whole blood was taken).

In one embodiment, the present plasma concentrate comprises platelets, from 5 to 400 mg/ml of fibrinogen, from 0.5 to 35 mg/ml of fibronectin, and a physiologically acceptable carrier comprising water and physiologically acceptable inorganic and organic ions in a physiologically acceptable concentration. In a preferred embodiment, the plasma concentrate is prepared from whole blood, and platelets are concentrated at least one-and-one-half times relative to the concentration of platelets in unconcentrated plasma from the same whole blood.

The present plasma concentrate may further contain a compound selected from the group consisting of an antibiotic, a collagen fleece, collagenase, hyaluronic acid, a wound-healing factor, zinc ions in an amount effective to decrease coagulation time of said plasma, and a biologically acceptable dye. A preferred biologically acceptable dye is disulphine blue, contained in an amount sufficient to visibly detect the plasma concentrate during its application to tissue. In a preferred embodiment, the plasma concentrate further comprises a pharmaceutically active compound, particularly an antibiotic to reduce the probability of infection by extraneous microorganisms.

The present invention also concerns a tissue sealant, comprising the present plasma concentrate and an activator. Preferably, the plasma concentrate in the present tissue sealant is platelet-rich plasma concentrate.

In one embodiment of the present tissue sealant, the activator is a mixture of thrombin and calcium in amounts sufficient to permit gelation of the plasma concentrate. In a further embodiment, the activator is autologous thrombin and platelets.

G. Apparatus for and Method of Mixing Two-Component Fibrin Sealant

Parallel syringes with the two components (e.g., concentrated platelet-rich plasma and calcium/thrombin solution) converge on a coaxial needle with mixing of the components at the application site, thus avoiding premature gelation; see FIG. 7. In the barrel of the syringe a cylindrical chamber 31 containing thrombin and calcium solution is surrounded by an annular chamber 32 containing concentrated platelet-rich plasma. Plunger 30 causes the solutions to exit the apparatus through coaxial needles and mix at the tip 36. An optional sleeve 34 ensures proper mixing, and may be retracted to expose premature gel for easy removal.

H. Dispenser/Activator for Platelet-Rich Plasma Concentrate

Most users of fibrin sealants have resorted to the use of bovine thrombin to induce gelation. In a preferred embodiment of the present invention, it is desirable to avoid excessive use of bovine proteins in the final preparation. Thus, a method and apparatus employing a small amount of bovine or other thrombogenic enzyme to trigger the autocatalytic activation of the coagulation process is envisioned. FIG. 8 shows a syringe 21 and applicator needle tip 23 separated by activator cartridge 22 through which platelet-rich plasma passes for activation by immobilized thrombin to convert fibrinogen to fibrin.

In a further optional embodiment, a needle designed to disrupt platelets may be used to apply a single-component concentrate (i.e., the concentrated plasma) without the use of thrombin. FIG. 8 shows a syringe 21 and applicator needle tip 23 separated by activator cartridge 22 through which platelet-rich plasma passes for activation by, e.g., nylon wool. In this embodiment, calcium is added to the concentrate immediately prior to or during its application to tissue in need of sealing.

A porous membrane or other material with high exposed surface to void volume ratio can be derivitized with thrombin or other thrombogenic or thrombin-like enzyme by known methods. The derivatized membrane is fitted between syringe and applicator needle.

In a separate but related embodiment, glass wool, nylon wool or collagen sponge or another material may be used in a similar configuration to cause eversion of the platelets, known to initiate coagulation.

In a separate but related embodiment, concentrated plasma may be kept cold to prevent gelation. After application, the heat of the living tissue will initiate gelation.

A big problem with prior precipitation methods is that the fibrinogen must be reconstituted. This is difficult and may take hours, and only a relatively low concentration is achievable. Thus not only does the present invention allow more rapid availability, a surgeon can decide that "this one is a bleeder" and have sealant in 15 minutes. Previous technology requires that the surgeon order fibrin glue before the procedure begins.

The present concentrated platelet-rich plasma can be left in the device until needed, for hours if necessary, without spontaneous gelation.

Other autologous precipitation methods require that blood be drawn days in advance to allow time so that there is time for processing. Besides the inconvenience, this procedure allows the possibility of tracking errors and thus infection.

Generally, a proteolysis inhibitor such as aprotinin is added to the fibrinogen component of fibrin glues. (Academic opinion is actually divided on whether this is necessary; need has never been proven rigorously.) The present methods for producing concentrated PRP retain the natural inhibitors which are evidently lost in precipitation steps.

Fibrinogen from fresh plasma produces a mechanically superior gel (based on the general properties of proteins damaged by precipitation). Platelets (contained in the present plasma concentrate) are useful for wound healing (many references available). Thus, an advantage of the present technology is that it provides better wound healing than conventional fibrin glues, which do not contain platelets.

Surgeons, particularly in the U.S., are likely to use bovine thrombin to "activate" the present tissue sealant. This is not a regulatory problem because bovine thrombin is available and is used routinely in surgery. However, the present invention provides a dispenser that activates prothrombin present in the concentrated platelet-rich plasma and/or that disrupt platelets so that clotting is initiated by one or more components in the concentrated plasma.

The present tissue sealant and autologous tissue sealant do more than merely seal the wound and adhere the damaged structures. In particular, the present autologous tissue sealant contains the patient's own living thrombocytes and wound healing factors, and thus, it nurtures the healing process. Other advantages of the present tissue sealant include the presence of attachment factors which (i) improve adhesion to damaged tissue and (ii) promote cellular infiltration. In the present autologous tissue sealant, which is made from the patient's own blood, important advantages include the ease, speed and convenience of preparation (it may be prepared in the operating room immediately before use). Furthermore, the optional absence of bovine thrombin in the present autologous tissue sealant avoids immune system and foreign body reactions and eliminates disease transmission (i.e., from the bovine thrombin source).

I. Separator and Method for Separating Particulates from Suspensions

In a further aspect of the present invention, a separator and a general method for separating particulates from suspensions is envisioned. Separating particulates from biological fluids (such as blood and plasma) is a common problem in the laboratory. A disposable cartridge containing a separation chamber (i.e., the first chamber in the apparatus used for preparing the present concentrated plasma) allows cellular and dense particle separation—basically anything that moves in response to centrifugal force.

Thus, the present apparatus for separating particulates from a liquid suspension comprises:

an inlet, a first chamber in fluid communication with the inlet, containing a first separator for separating particulates from the liquid suspension, thus forming a particulate-free liquid, and an outlet for withdrawing the liquid.

A "particulate-free liquid" is one which is substantially free of insoluble particles, preferably those insoluble particles having an average size above a pre-selected value (e.g., from 500 to 20μ, or any value for which filters or other devices are available for removing such insoluble particles; e.g., 250μ, 100μ, 80μ, 50μ, etc.).

J. Concentrator and Method for Concentrating Macromolecule Solutions

In an even further aspect of the present invention, a concentrator and method for concentrating macromolecule solutions based on the design of the concentrator (or second) chamber used in the apparatus for preparing the present concentrated plasma is envisioned. SEPHADEX (trademark, Pharmacia), for example, is rarely used for concentrating macromolecule solutions. The device may not concentrate to dryness, but is useful for concentration of proteins (or any high molecular weight solution), preferably by a factor of three times or a multiple of three times, depending on the number of concentrator chambers in the apparatus.

Thus, the present apparatus for concentrating a solution of a substance having a molecular weight greater than a predetermined value (i.e., macromolecule solution) comprises:

an inlet, a chamber in fluid communication with the inlet, containing a concentrator for concentrating the solution and a separator for separating the solution from the concentrator, and an outlet for withdrawing the concentrated solution.

Other features of the invention will become apparent in the course of the following descriptions of exemplary embodiments which are given for illustration of the invention and are not intended to be limited thereof.

EXAMPLE 1

Using a cartridge as shown in either FIGS. 1, 2, 3 or 4, and following the procedure below, a concentrated platelet-rich plasma and tissue sealant can be prepared:

I. Collect blood from patient using standard citrate anticoagulant.

II. Inject a standard quantity of blood (e.g., 50 cc) in to the blood fill port of the disposable cartridge. The cartridge is sealed making contamination impossible. It will be used in the operating room making tracking errors impossible.

III. The operator then starts the microprocessor-controlled centrifuge by push-button. All remaining steps until removal of the concentrate are automatic.

IV. (Optional step for designs incorporating free concentrator beads, FIG. 2) The centrifuge rotates briefly clockwise then counterclockwise a few times at a speed sufficient to evenly distribute the free dextranomer beads outside the concentrator cup lip.

V. The centrifuge spins at 3,000 rpm for one to ten minutes to separate platelet-rich plasma from cells. The whole blood passes through a pore in the blood receiver chamber into the separation chamber.

VI. The centrifuge stops for 15-90 seconds. Under the force of gravity the platelet-rich plasma passes into the lower chamber, or concentrator chamber, (optionally by going through a through a hydrophilic filter, appropriate when free beads are present in the concentrator chamber as in FIG. 2).

VII. In the concentrator chamber platelet-rich plasma comes into contact with beads bonded by electrostatic force to an open is cell foam (cartridge of FIGS. 1 and 3), free concentrator beads (cartridge of FIG. 2), or beads embossed onto discs (cartridge of FIG. 4). Slow rotation of the centrifuge aids mixing. The porosity and hydrophobicity of the porous wall are such that the low centrifugal force generated is not sufficient to overcome surface tension and the plasma remains within the compartment at the inner surface. The beads swell with water, ions and low molecular weight proteins (i.e., those proteins having a molecular weight below the cutoff value). The pore size of the beads is so chosen that the proteins become concentrated in the space around the beads. The quantity of beads is chosen so that the platelet-rich plasma is concentrated the desired amount, e.g., 3×. When using DEBRISAN, approximately 2.6 gm is required per 10 cc plasma to achieve 3-fold concentration. The protein concentrate contains the same ion concentrations as the unconcentrated plasma.

VIII. The rate of rotation is increased forcing the concentrated platelet-rich plasma out through the filter into the outer compartment.

IX. The centrifuge stops, and under the force of gravity concentrated platelet-rich plasma collects in the bottom. The concentrated platelet-rich plasma may be left for extended periods (hours) without spontaneous gelation.

X. Concentrated platelet-rich plasma is removed into a syringe.

XI. (Optional.) Thrombin/calcium solution is prepared separately.

XII. Using a variety of methods described in the literature for cryoprecipitated fibrinogen, the two solutions are combined and rapidly gel to form the TISSUE SEALANT.

XIII. (Optional; substitute for XI and XII.) Using a needle tip designed to disrupt platelets, a single-component concentrate may be applied without the use of bovine thrombin.

A comparison of the properties of the present tissue sealant and prior tissue sealant prepared from cryoprecipitated fibrin is shown in the Table below:

TABLE

Concentrations of Tissue Sealant Compositions

| Blood Component | Precipitate Fibrin Glue | Autologous Concentrated PRP (3×) |
| --- | --- | --- |
| Ions | per reconstitution solution | identical to patient plasma |
| Platelets | none concentration | 3× plasma |
| Proteins | only proteins that cryoprecipitate; fibrinogen, factor XIII, fibronectin, albumin, plasminogen | all plasma proteins at normal (less than 5 kDa) or 3× normal (more than 5 kDa) concentrations |
| Albumin | 10–25 mg/ml | 100–165 mg/ml |
| Factor XIII | 75 µg/ml | 30–60 µg/ml |
| Fibrinogen | 70–110 mg/ml | 5–14 mg/ml |
| Fibronectin | 2–9 mg/ml | 0.5–1.2 mg/ml |
| Plasminogen | 20–60 µg/ml | 600 µg/ml |
| Aprotinin | 1,500 KIU/ml | 0 KIU/ml |

The present tissue sealant also appears to show similar tensile strength to that of cryoprecipitated fibrin tissue sealant. The adhesive strength provided by the present tissue sealant is believed to be superior to that of cryoprecipitated fibrin tissue sealant because fibrinogen and other important proteins are not denatured by the present process.

A key advantage of the present invention is the presence of platelets. Adhesion of the platelets to collagen III fibrils leads to platelet aggregation, promoted by 5-hydroxytryptamine and epinephrine released from the platelets. Other growth and healing factors are released by the platelets. Platelet-derived growth factor is a mitogen for fibroblasts and smooth muscle cells. Platelet factors stimulate neovascularization, especially when the area is anoxic. Platelets also make fibrin more resistant to mechanical shear forces and to fibrinolysis.

It is possible that for certain applications lesser numbers of platelets may be desirable. The invention may be adjusted to achieve this outcome. Because of their low mass compared with other blood cells, a preponderance of platelets is preserved in the final products when conditions are chosen to minimally separate the bulk of said more massive cells from whole blood. For example, a 4-inch diameter cartridge, 1 inch in height and fitted with a sintered plastic wall as in FIG. 2 will separate most of the blood cells from 50 cc of whole blood when centrifuged for 3 minutes at 2,000 rpm. By increasing the speed to 5,000 rpm and the time to 15 minutes, most of the platelets are also sedimented through the porous walls to yield plasma depleted of platelets. Such platelet depleted plasma may be desirable if, for example, it were desired that the plasma or concentrate derived therefrom should be processed by filtration through a sterile submicron membrane to render the final product suitable for storage for an extended time (days).

Obviously, numerous modifications and variations of the present invention are possible in light of the above teachings. It is therefore to be understood that within the scope of the appended claims, the invention may be practiced otherwise than as specifically described herein.

45. See, for example, DelRossi, A. J., A. C. Cernaianu, R. A. Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (2 1990): 281–6.

What is claimed as new and is desired to be secured by Letters: Patent of the United States is:

1. A method for concentrating blood plasma, comprising:

(a) removing water and proteins from said plasma by contacting said plasma with a concentrator having a molecular weight cutoff of from 2 to 100 kDa to provide concentrated plasma, proteins being removed having a molecular weight smaller than the molecular weight cutoff of said concentrator; and (b) separating said concentrated plasma from said concentrator.

2. The method of claim 1, wherein said concentrator comprises a material selected from the group consisting of a dextranomer, SEPHADEX, dextramine, polyacrylamide, BIO-GEL P, silica gel, a zeolite, DEBRISAN, cross-linked agarose, starch and alginate gel, either in free bead form or attached to a matrix or embedded into a disc.

3. The method of claim 1, wherein, prior to said contacting step (a), said concentrator is dry.

* * * * *

UNITED STATES PATENT AND TRADEMARK OFFICE
CERTIFICATE OF CORRECTION

PATENT NO. : 5,788,662
DATED : August 4, 1998
INVENTOR(S) : Richard D. Antanavich, Randel Dorian It is certified that error appears in the above-identified patent and that said Letters Patent is hereby corrected as shown below:

On the Title Page [63] after "Patent No.," delete [5,585,008] and insert --5,585,007--.

Signed and Sealed this

Tenth Day of April, 2001

Attest:

NICHOLAS P. GODICI

*Attesting Officer*   *Acting Director of the United States Patent and Trademark Office*